(12) United States Patent
Rock et al.

(10) Patent No.: US 11,975,206 B2
(45) Date of Patent: May 7, 2024

(54) MULTI-ELECTRODE IMPLANTABLE MEDICAL DEVICE (IMD)

(71) Applicant: Medtronic, Inc., Minneapolis, MN (US)

(72) Inventors: Kaileigh E. Rock, Saint Paul, MN (US); Michael D. Eggen, Chisago City, MN (US); Jean M. Carver, Blaine, MN (US); Duane N. Mateychuk, Ramsey, MN (US); Zhongping C. Yang, Woodbury, MN (US); Douglas S. Hine, Forest Lake, MN (US); Scott J. Brabec, Elk River, MN (US); Vania Lee, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 38 days.

(21) Appl. No.: 17/191,071

(22) Filed: Mar. 3, 2021

(65) Prior Publication Data
US 2021/0275824 A1   Sep. 9, 2021

Related U.S. Application Data

(60) Provisional application No. 62/986,416, filed on Mar. 6, 2020.

(51) Int. Cl.
  *A61N 1/368*  (2006.01)
  *A61N 1/05*   (2006.01)
  *A61N 1/375*  (2006.01)

(52) U.S. Cl.
  CPC ....... *A61N 1/37512* (2017.08); *A61N 1/0573* (2013.01); *A61N 1/368* (2013.01); *A61N 1/37518* (2017.08); *A61N 1/3756* (2013.01)

(58) Field of Classification Search
  CPC .. A61N 1/37512; A61N 1/0573; A61N 1/368; A61N 1/37518; A61N 1/3756; A61N 2001/058; A61N 1/37205
  See application file for complete search history.

(56) References Cited

U.S. PATENT DOCUMENTS

| 3,814,104 A | 6/1974 | Irnich et al. |
| 3,835,864 A | 9/1974 | Rasor et al. |

(Continued)

FOREIGN PATENT DOCUMENTS

| WO | 2002022202 A2 | 3/2002 |
| WO | 2006118865 A2 | 11/2006 |

(Continued)

OTHER PUBLICATIONS

Haqqani et al., "The Implantable Cardioverter-Defibrillator Lead: Principles, Progress and Promises," PACE, vol. 32, Oct. 2009, pp. 1336-1353.

(Continued)

*Primary Examiner* — Eugene T Wu
(74) *Attorney, Agent, or Firm* — Shumaker & Sieffert, P.A.

(57) ABSTRACT

An implantable medical device (IMD) comprises a plurality of deep tines configured to be advanced into a septum of a heart of a patient in different directions that are not parallel to a longitudinal axis of the implantable medical device, wherein each deep tine of the plurality of deep tines is configured to deliver cardiac pacing to cardiac tissue distal to a chamber of the heart in which the IMD is implanted, and one or more shallow electrodes engageable with the septum, wherein the one or more shallow electrodes are configured to deliver cardiac pacing to the chamber of the heart in which the IMD is implanted.

10 Claims, 20 Drawing Sheets

(56) References Cited

U.S. PATENT DOCUMENTS

| | | | |
|---|---|---|---|
| 3,943,936 A | 3/1976 | Rasor et al. | |
| 4,103,690 A | 8/1978 | Harris | |
| 4,142,530 A | 3/1979 | Wittkampf | |
| 4,256,115 A | 3/1981 | Bilitch | |
| 4,269,198 A | 5/1981 | Stokes | |
| 4,280,512 A | 6/1981 | Karr et al. | |
| 4,858,623 A | 8/1989 | Bradshaw et al. | |
| 4,936,823 A | 6/1990 | Colvin | |
| 5,193,540 A | 3/1993 | Schulman et al. | |
| 5,411,535 A | 5/1995 | Fujii et al. | |
| 5,487,758 A * | 1/1996 | Hoegnelid | A61N 1/0573 607/123 |
| 5,573,540 A | 11/1996 | Yoon | |
| 5,674,259 A | 10/1997 | Gray | |
| 5,683,447 A | 11/1997 | Bush et al. | |
| 6,007,558 A | 12/1999 | Ravenscroft et al. | |
| 6,151,525 A | 11/2000 | Soykan et al. | |
| 6,212,434 B1 | 4/2001 | Scheiner | |
| 6,240,322 B1 | 5/2001 | Peterfeso et al. | |
| 6,286,512 B1 | 9/2001 | Loeb et al. | |
| 6,409,674 B1 | 6/2002 | Brockway et al. | |
| 6,575,967 B1 | 6/2003 | Leveen et al. | |
| 6,643,546 B2 | 11/2003 | Mathis et al. | |
| 6,783,499 B2 | 8/2004 | Schwartz | |
| 6,915,149 B2 | 7/2005 | Ben-Haim | |
| 6,978,178 B2 | 12/2005 | Sommer et al. | |
| 7,082,335 B2 | 7/2006 | Klein et al. | |
| 7,139,614 B2 | 11/2006 | Scheiner et al. | |
| 7,290,743 B2 | 11/2007 | Nowack | |
| 7,412,289 B2 | 8/2008 | Malonek et al. | |
| 7,418,298 B2 | 8/2008 | Shiroff et al. | |
| 7,813,805 B1 | 10/2010 | Farazi | |
| 8,353,940 B2 | 1/2013 | Benderev | |
| 8,781,605 B2 | 7/2014 | Bornzin et al. | |
| 9,017,341 B2 | 4/2015 | Bornzin et al. | |
| 9,039,594 B2 | 5/2015 | Annest et al. | |
| 9,597,514 B2 | 3/2017 | Khairkhahan et al. | |
| 9,901,732 B2 | 2/2018 | Sommer et al. | |
| 10,039,922 B2 | 8/2018 | Regnier | |
| 10,159,834 B2 | 12/2018 | Drake et al. | |
| 10,406,370 B1 | 9/2019 | Makharinsky | |
| 10,413,720 B2 | 9/2019 | Nuta et al. | |
| 10,493,284 B2 | 12/2019 | Ortega et al. | |
| 10,729,902 B1 | 8/2020 | Makharinsky et al. | |
| 10,792,080 B2 | 10/2020 | Raina et al. | |
| 2002/0103424 A1 | 8/2002 | Swoyer et al. | |
| 2002/0165589 A1 | 11/2002 | Imran et al. | |
| 2003/0060866 A1 | 3/2003 | Schmidt | |
| 2003/0088301 A1 | 5/2003 | King | |
| 2004/0122456 A1 | 6/2004 | Saadat et al. | |
| 2004/0147973 A1 | 7/2004 | Hauser | |
| 2004/0230281 A1 | 11/2004 | Heil et al. | |
| 2006/0084965 A1 | 4/2006 | Young | |
| 2006/0085039 A1 | 4/2006 | Hastings et al. | |
| 2006/0085041 A1 | 4/2006 | Hastings et al. | |
| 2006/0224224 A1 * | 10/2006 | Muhlenberg | A61N 1/0587 607/122 |
| 2007/0179552 A1 | 8/2007 | Dennis et al. | |
| 2009/0082828 A1 | 3/2009 | Ostroff | |
| 2010/0318172 A1 | 12/2010 | Schaefer | |
| 2012/0172892 A1 | 7/2012 | Grubac et al. | |
| 2014/0039591 A1 | 2/2014 | Drasler et al. | |
| 2014/0066895 A1 | 3/2014 | Kipperman | |
| 2014/0107723 A1 * | 4/2014 | Hou | A61N 1/3756 607/9 |
| 2015/0039070 A1 | 2/2015 | Kuhn et al. | |
| 2015/0335894 A1 | 11/2015 | Bornzin et al. | |
| 2017/0326369 A1 * | 11/2017 | Koop | A61N 1/0573 |
| 2018/0050208 A1 | 2/2018 | Shuros et al. | |
| 2019/0083779 A1 | 3/2019 | Yang et al. | |
| 2019/0111265 A1 | 4/2019 | Zhou | |
| 2019/0111270 A1 | 4/2019 | Zhou | |
| 2019/0143118 A1 | 5/2019 | Bullinga | |
| 2019/0192863 A1 | 6/2019 | Koop et al. | |
| 2019/0209845 A1 | 7/2019 | Stadler et al. | |
| 2019/0232053 A1 | 8/2019 | Yang et al. | |
| 2019/0269420 A1 | 9/2019 | Matusaitis et al. | |
| 2019/0351236 A1 | 11/2019 | Koop | |
| 2019/0374254 A1 | 12/2019 | Arevalos et al. | |
| 2020/0229805 A1 | 7/2020 | Gammie et al. | |
| 2020/0229806 A1 | 7/2020 | Goldfarb et al. | |
| 2020/0261725 A1 | 8/2020 | Yang et al. | |
| 2020/0261734 A1 | 8/2020 | Yang et al. | |
| 2020/0289829 A1 | 9/2020 | Ghosh | |
| 2020/0306522 A1 | 10/2020 | Chen et al. | |
| 2020/0306530 A1 | 10/2020 | Koop et al. | |
| 2020/0353249 A1 | 11/2020 | Min et al. | |
| 2020/0353265 A1 | 11/2020 | Ghosh et al. | |
| 2021/0046306 A1 | 2/2021 | Grubac et al. | |
| 2022/0314001 A1 | 10/2022 | Bonner et al. | |
| 2022/0387764 A1 | 12/2022 | Bonner et al. | |
| 2023/0012417 A1 | 1/2023 | Rock et al. | |

FOREIGN PATENT DOCUMENTS

| | | |
|---|---|---|
| WO | 2018097826 A1 | 5/2018 |
| WO | 2020023406 A1 | 1/2020 |
| WO | 2020076833 A1 | 4/2020 |
| WO | 2020163031 A1 | 8/2020 |

OTHER PUBLICATIONS

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

International Search Report and Written Opinion of International Application No. PCT/US2021/021026, dated Jun. 9, 2021, 8 pp.

U.S. Appl. No. 16/847,315, filed Apr. 13, 2020, naming inventors Drake et al.

U.S. Appl. No. 16/895,133, filed Jun. 8, 2020, naming inventors Anderson et al.

U.S. Appl. No. 17/125,250, filed Dec. 17, 2020, naming inventors Ries et al.

Austin et al., "Innovative pacing: Recent advances, emerging technologies, and future directions in cardiac pacing", Trends in Cardiovascular Medicine, vol. 26, Mayo Clinic Florida, 2016, pp. 452-463, (Applicant points out, in accordance with MPEP 609.04(a), that the year of publication, 2016, is sufficiently earlier than the effective U.S. filing date, so that the particular month of publication is not an issue.).

Hayes, "Advances in pacing therapy for bradycardia", International Journal of Cardiology, vol. 32, Elsevier Science Publishers B.V., Apr. 1, 1991, pp. 183-196.

Mulpuru et al., "Cardiac Pacemakers: Functions, Troubleshooting, and Management", Journal of the American College of Cardiology, vol. 69, No. 2, Oct. 18, 2016, pp. 189-210.

Petrie, "Permanent Transvenous Cardiac Pacing", Clinical Techniques in Small Animal Practice, Elsevier Inc., 2005, pp. 164-172, (Applicant points out, in accordance with MPEP 609.04(a), that the year of publication, 2005, is sufficiently earlier than the effective U.S. filing date, so that the particular month of publication is not an issue.).

* cited by examiner

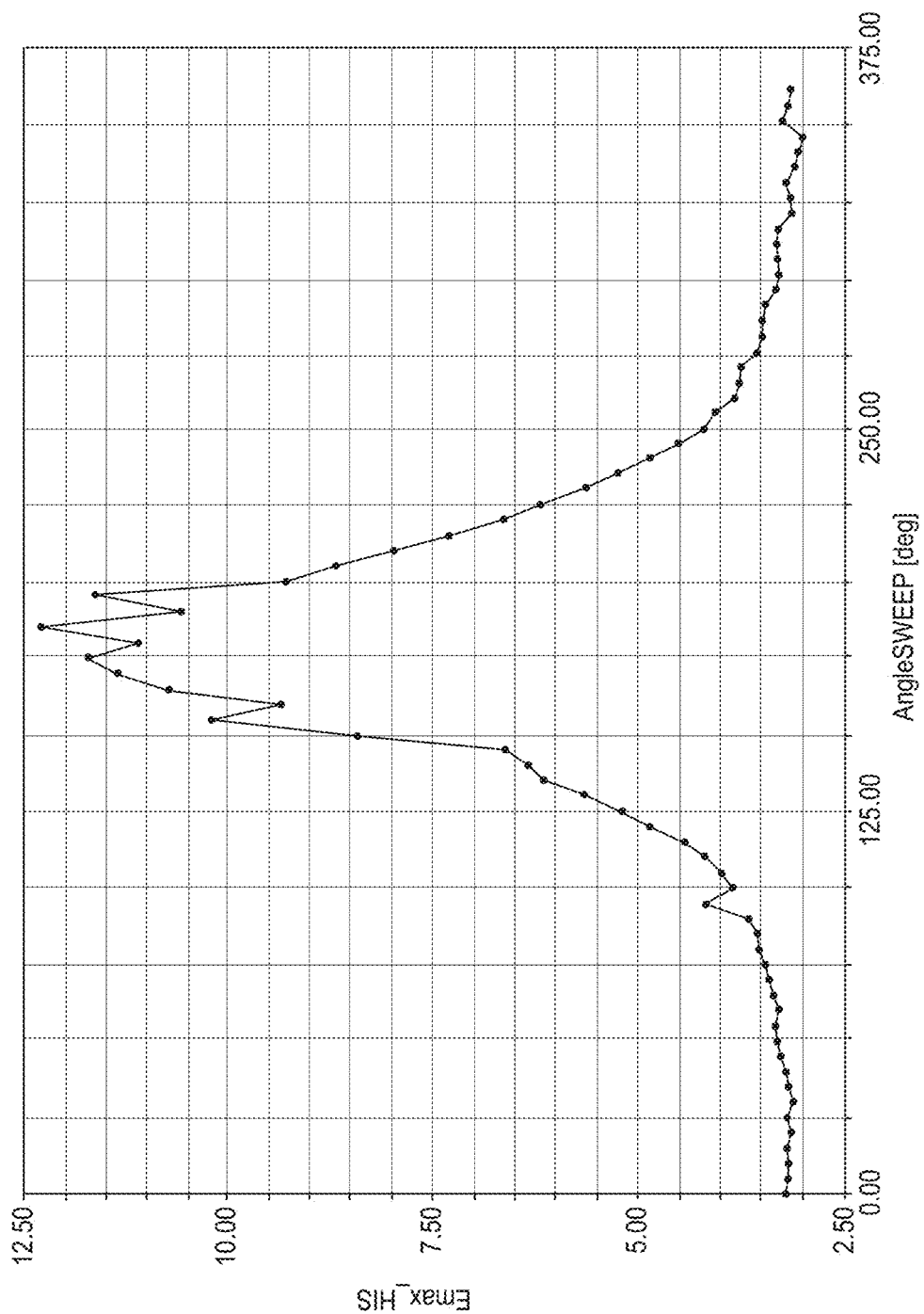

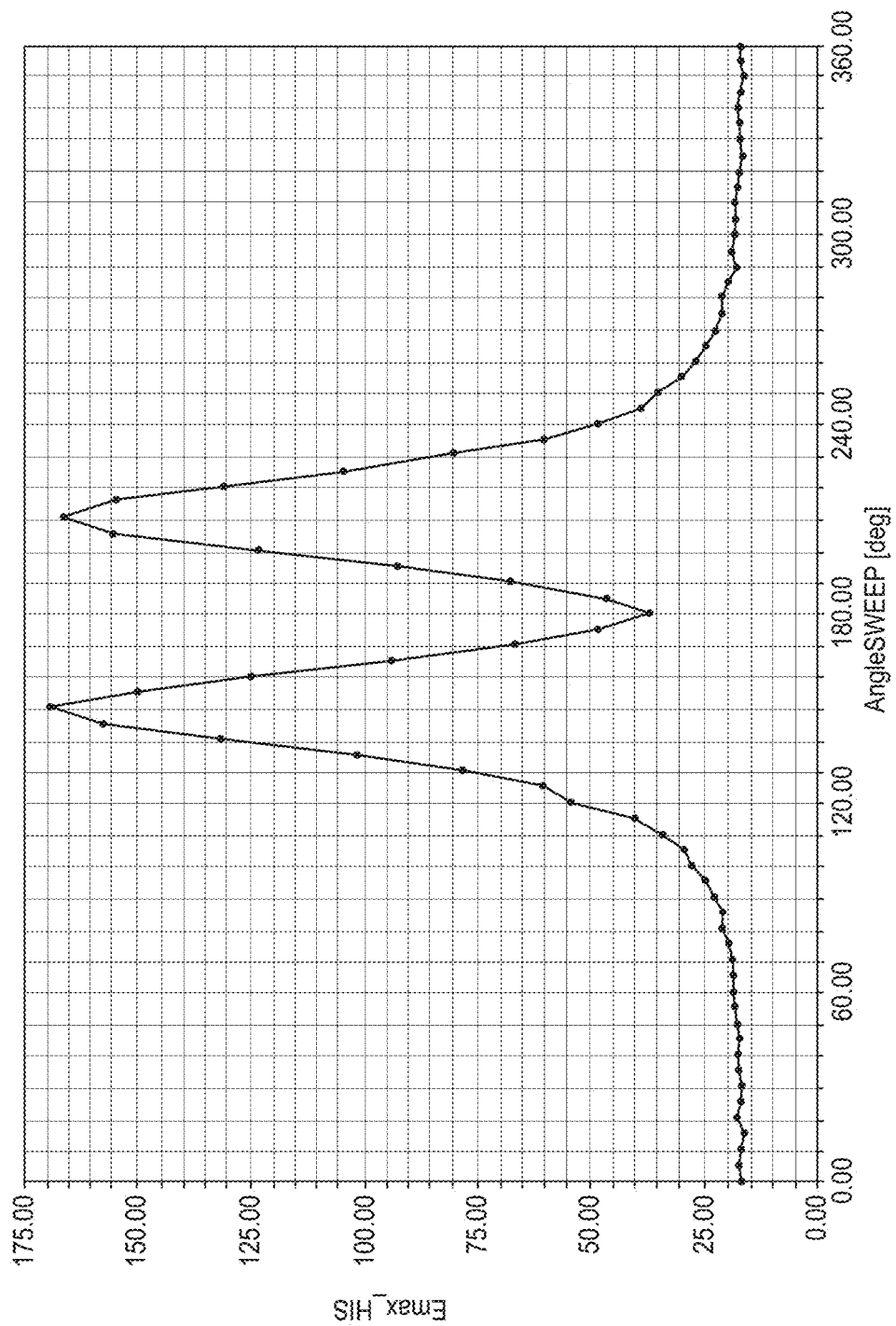

MULTI-ELECTRODE IMPLANTABLE MEDICAL DEVICE (IMD)

This application claims the benefit of U.S. Provisional Application Ser. No. 62/986,416, filed Mar. 6, 2020, the entire content of which is incorporated herein by reference.

TECHNICAL FIELD

This disclosure is related to medical device systems, such as multi-electrode implantable medical devices (IMDs), designed to provide pacing pulses directly or indirectly to selected cardiac tissue, such as the bundle of His of a patient's heart.

BACKGROUND

In some examples, implantable cardiac pacemakers include a pulse generator device to which one or more flexible elongated lead wires are coupled. The pulse generator device may be implanted in a subcutaneous pocket, remote from the patient's heart, and each of the one or more lead wires extends therefrom to a corresponding electrode, coupled thereto and positioned at a pacing site, either endocardial or epicardial. Relatively compact implantable medical devices (IMDs), sometimes referred to as leadless pacing devices or intracardiac pacing devices, have also been developed that are wholly contained within a relatively compact package, the entirety of which is configured for implant in close proximity to the pacing site, e.g., within a chamber of the patient's heart.

SUMMARY

This disclosure describes fixation mechanisms and electrode configurations for IMDs, such as relatively compact IMDs, as well as for IMDs including elongated implantable medical leads. As used in this description, the term "IMD" may refer to the entire IMD itself, or a portion thereof. As one example, this disclosure may use the term "IMD" to refer to the entirety of a relatively compact IMD suitable for implantation within a chamber of a patient's heart. As another example, this disclosure may use the term "IMD" to refer to the distal portion of an elongated lead that can be affixed to a target tissue (e.g., heart tissue) to sense electrical data from or to deliver pacing pulses or neurostimulation pulses to the target tissue. For example, the electrode configurations of this disclosure are applicable to both the distal portion of an elongated lead, as well as to relatively compact IMDs suitable for in-chamber implantation.

Electrode configurations of this disclosure provide a plurality of electrode options for application of pacing therapy to a target cardiac tissue other than the heart chamber in which the IMD is implanted, e.g., to steer applied pacing therapy via the bundle of His. In contrast, currently available lead designs require the clinician (e.g., implant physician) to place the lead electrodes as close as possible physically to the bundle of His to deliver His pacing therapy.

Various examples of this disclosure are directed to lead or compact IMD designs that leverage one or more fixation components as electrodes. By using one or more fixation components as electrodes, the configurations of this disclosure leverage the placement of the fixation components in the interatrial septum or the interventricular septum or the atrioventricular septum of the heart to steer pacing therapy using one or more electrodes that are placed physically close to target cardiac tissue, such as the bundle of His. Fixation components/electrodes of this disclosure include one or more of helical fixation components, tines, and various other examples. When deployed, the fixation components of this disclosure may provide improved tissue fixation, improved penetration to a selected depth within a tissue (e.g., any of the septums/septa listed above), improved electrode contact with selected tissues, and pacing therapy that is more precisely applied to the bundle of His or other target cardiac tissue.

In one example, this disclosure is directed to an IMD that includes a plurality of deep tines and one or more shallow electrodes. The deep tines are configured to be advanced into a septum of a heart of a patient in different directions that are not parallel to a longitudinal axis of the implantable medical device, wherein each of the plurality of tines is configured to deliver cardiac pacing to cardiac tissue distal to a chamber of the heart in which the IMD is implanted. The one or more shallow electrodes are engageable with the septum. Some or all of the one or more shallow electrodes are configured to deliver cardiac pacing to the chamber of the heart in which the IMD is implanted.

In another example, this disclosure is directed to an IMD that includes a deep electrode and a plurality of shallow tines. The deep electrode is configured to be advanced into a septum of a heart of a patient. The shallow tines are engageable with the septum. A subset of the shallow tines are selectable to form one or more return electrodes configured to deliver, in tandem with the helical lead electrode, pacing therapy to a target site within the septum.

In another example, a method comprises advancing an inner lead that is moveable within a lumen of an outer lead toward a target site of a heart of a patient; engaging the target site with an electrode at a distal end of the inner lead; and advancing the outer lead toward the target site of the heart of the patient to cause a plurality of deep tines at a distal end of the outer lead to pierce a septum at the target site of the heart.

The details of one or more examples are set forth in the accompanying drawings and the description below. Other features, objects, and advantages will be apparent from the description and drawings, and from the claims.

BRIEF DESCRIPTION OF DRAWINGS

FIGS. 4A-4F are graphs illustrating electric field variance at a bundle of His as respective functions of angular sweeps in a computer-modeled simulation done on IMD configurations shown in FIGS. 3A-3F.

DETAILED DESCRIPTION

Figure 1:
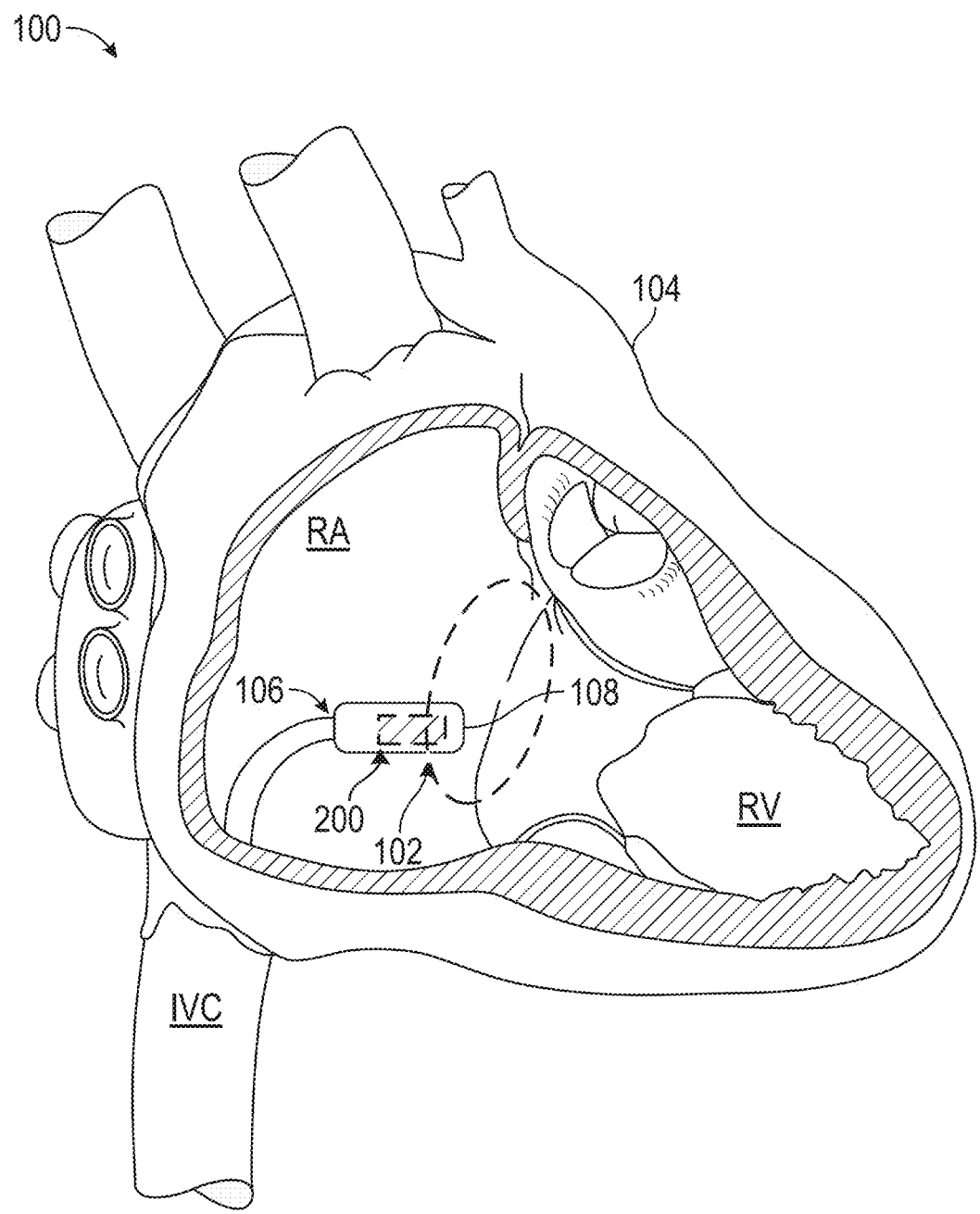
FIG. 1 is a conceptual diagram illustrating a portion of an example medical device system configured to implant a relatively compact implantable medical device at a target implant site.

This disclosure describes implantable medical devices (IMDs) having electrode configurations that enable a clinician to select electrodes to target delivery of pacing pulses to selected cardiac tissue, such as the His bundle (hereinafter, "HB") of a patient's heart. The HB is a collection of heart muscle cells specialized for electrical conduction. As part of the electrical conduction system of the heart, the HB transmits electrical impulses from the atrioventricular node (located between the atria and the ventricles) via bundle branches of the HB. These transmitted impulses indirectly provide electrical conduction to the ventricles of the heart, causing the cardiac muscle of the ventricles to depolarize and, in turn, contract at a regular interval. To cause electrical depolarization of a ventricle of the heart (i.e., to effect "capture"), pacing via the HB must have a sufficient electric field strength, e.g., exceeding one Volt per centimeter or one hundred Volts per meter (1V/cm or 100V/m).

Although described herein primarily in the context of targeting the HB, the electrode configurations described herein may be used to any target cardiac tissue that is relatively deeper than or remote from the wall tissue of the chamber in which the IMD is implanted. Examples include targeting the HB, right bundle branch (RBB), left bundle branch (LBB), or other ventricular tissue using an IMD implanted within an atrium, such as the right atrium. Other examples include targeting the HB or other cardiac tissue using an IMD implanted within a ventricle, such as the right ventricle. Targeting portions of the conduction system of the heart for pacing, such as the HB and bundle branches, may be referred to as conduction system pacing.

The electrode configurations of this disclosure may be implemented in IMDs that include a housing coupled to one or more elongated leads, or in relatively compact IMDs that are sufficiently small to be implanted within a chamber of the patient's heart. In examples of this disclosure that are implemented in an IMD with a housing coupled to one or more elongated leads, the "housing" may also be referred to as a "can," and the "elongated leads" may refer to respective leads with a distal end having electrode(s). According to several configurations of this disclosure, a distal electrode is positioned within the septum of the patient's heart, e.g., relatively close to the HB. One or more return electrodes are positioned relative to the septum-embedded electrode such that the clinician can steer pacing therapy to the HB using a combination of the distal electrode and one or more of the return electrodes. The distal electrode, which is typically embedded in the septum upon implantation, is described as being positioned at the distal end of the IMD or lead coupled to the IMD. The electrodes of the IMD may be configured to, upon IMD implantation, sense electrical signals from tissue and/or deliver electrical therapies to the tissue, such as to the HB of the patient's heart.

Some electrode configuration examples according to this disclosure additionally or alternatively include a plurality of distal electrodes. The distal electrodes may be configured such that their electrically active portions, e.g., distal ends, are spaced apart from one another in the cardiac tissue. Some configurations of this disclosure include exposed electrically active parts at locations along the tines that are not limited to the distal tips of the tines. In this manner, the likelihood that at least one of the distal electrodes is proximate to or within a target tissue may be increased, and/or multiple target tissues may be sensed or stimulated. In some examples, the distal electrodes may be individually controlled to deliver electrical stimulation, and an IMD may select which one or more of the distal electrodes is used to stimulate target tissue. In some examples, the plurality of distal electrodes comprise a plurality of tines that extend, e.g., are curved to extend, in different directions from the distal end of the IMD or lead.

An example fixation component for the IMD, e.g., to fix the relatively compact IMD housing or lead distal end to cardiac tissue of the heart chamber in which it is implanted, may include a base and a plurality of fixation tines. The fixation tines may act as return electrodes in some examples. The fixation tines may act as electrodes for pacing and sensing in the implant chamber, e.g., atrial pacing and sensing, in some examples.

In this disclosure, the example systems, devices, and techniques will be described with reference to delivering electrodes of an IMD configured as a cardiac pacemaker to a target site (namely, the HB) in the heart of a patient. However, it will be understood that example systems, devices, and techniques of the present disclosure are not limited to delivering such IMD electrodes to this particular target site in the heart. For example, the example systems, devices, and techniques described herein may be used to deliver other medical devices, such as sensing devices, neurostimulation device, medical electrical leads, etc. Additionally, the example systems, devices, and techniques described herein may be used to deliver any such IMDs to other locations within the body of the patient. In short, the example systems, devices, and techniques described herein can find useful application in delivery of a wide variety of implantable medical devices for delivery of therapy to a patient or patient sensing.

FIG. 1 is a conceptual diagram illustrating a portion of an example medical device system 100 configured to implant a relatively compact implantable medical device 200 ("IMD 200") at a target implant site 102. In some examples, as illustrated in FIG. 1, the target implant site 102 may include an appendage or triangle of Koch region of a right atrium (RA) of the heart 104 of a patient. In some examples, target implant site 102 may include other portions of heart 100, such as an interventricular septum, or other locations within a body of the patient. Medical device system 100 may include a delivery tool 106 configured to house and controllably deploy relatively compact IMD 200. In some examples, a clinician may maneuver medical device system 100 to target implant site 102. For example, with the IMD loaded therein, the clinician may guide delivery tool 106 up through the inferior vena cava (IVC) and into the RA of heart 104. In some examples, other pathways or techniques may be used to guide delivery tool 106 into other target implant sites within the body of the patient.

Figure 2A:
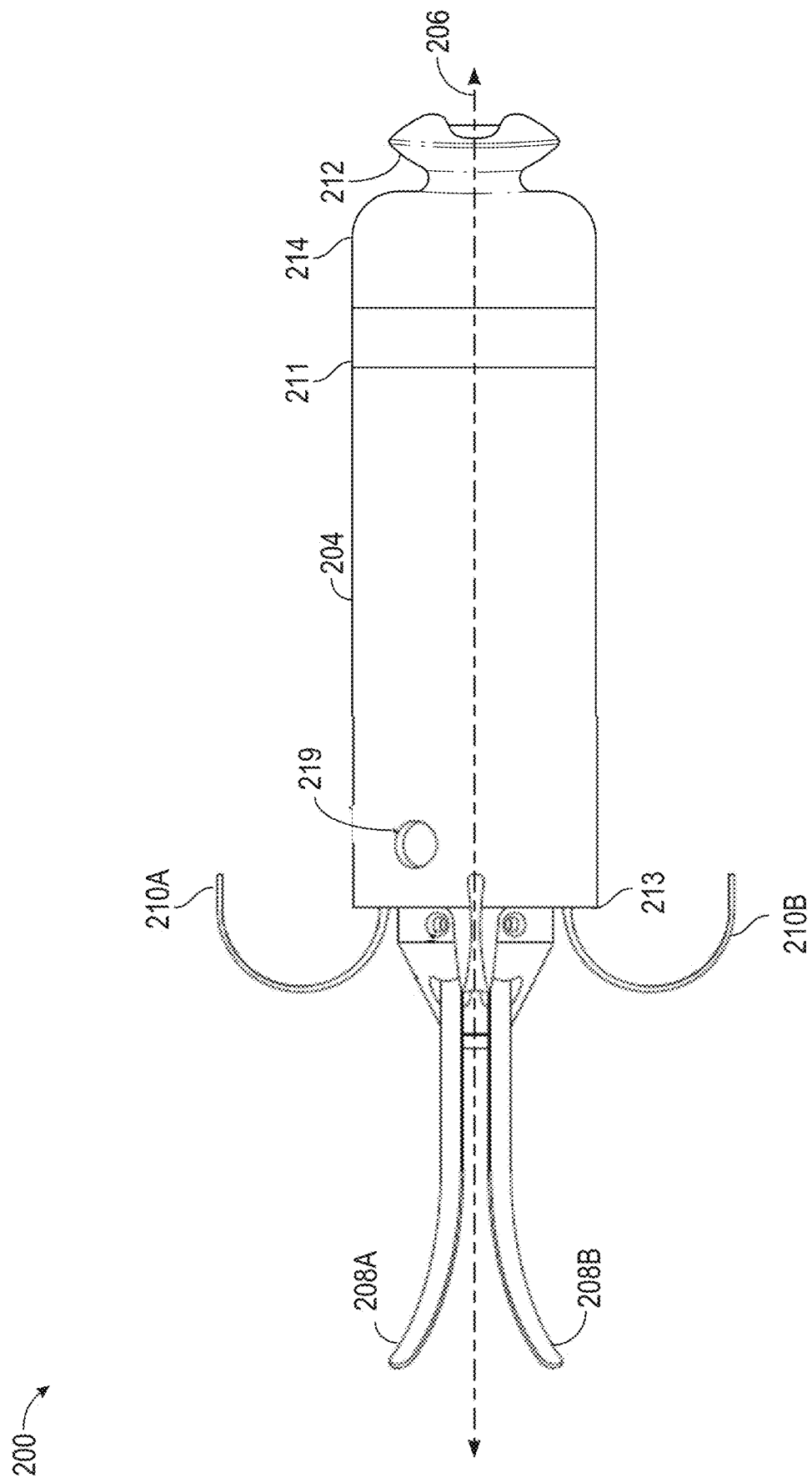
FIG. 2A is a conceptual diagram illustrating a plan view of an example of a relatively compact IMD including an electrode configuration according to the techniques of this disclosure.

FIG. 2A is a conceptual diagram illustrating a plan view of an example relatively compact IMD 200 including an electrode configuration according to the techniques of this disclosure. FIG. 2A is described as illustrating a "plan view" in that FIG. 2A illustrates a projection of IMD 200 on a horizontal plane. IMD 200 includes housing 204 extending along longitudinal axis 206 from a proximal end to a distal end. Housing 204 may be formed from a biocompatible and biostable metal such as titanium. In some examples, housing 204 may include a hermetically sealed housing. Housing 204 may include a nonconductive coating and define a return electrode 211 as an uncoated portion of housing 204. IMD 200 may include any suitable dimensions. In some examples, an outer diameter of IMD 200 (e.g., outer diameter of housing 204) may be between about 10 French (Fr) and about 30 Fr, such as about 20 Fr.

IMD 200 may incorporate electronic circuitry, including one or more of sensing circuitry (e.g., for sensing cardiac signals), therapy delivery circuitry (e.g., for generating cardiac pacing pulses), and processing circuitry for controlling the functionality of IMD 200, and may include deep tines 208 and shallow tines 210. As used, herein, a "tine" refers to an elongated element that extends from the distal end of housing 204, which may be linear or nonlinear. In various examples in accordance with this disclosure, a "tine" may have elastic or superelastic properties, and may, in some cases, be configured to pierce and potentially penetrate into or through target tissue. In some examples, deep tines 208 and/or shallow tines 210 may be coupled to or integrated with a base fixedly attached to the distal end of IMD 200.

In some examples, one or both of deep tines 208, when activated, may function as a distal electrode. In their respective deformed states, deep tines 208 extend to a greater distance from the distal end of housing 204 along longitudinal axis 206 than the distance to which shallow tines 210 extend from the distal end of housing 204 along longitudinal axis 206. When deployed in the target tissue (e.g., a cardiac septum), in their respective deployed, e.g., relaxed or deformed, states, deep tines 208 may extend further into the target tissue than the depth to which shallow tines 210 extend into the target tissue. In some examples, deep tines 208, in their respective deployed states, may pierce through or penetrate the entire thickness of the target tissue, potentially reaching a heart chamber opposite the septum from the chamber of implantation of IMD 200, while shallow tines 210, in their respective deployed states, may pierce the septum partially without reaching the chamber opposite the septum from the chamber of implantation of IMD 200.

Each of deep tines 208 may include a conductor, such as an electrically conductive material, having a non-conductive coating, such as polytetrafluoroethylene (PTFE), a portion of the conductive material, e.g., a distal end of the deep tine, being exposed to the tissue in which deep tines 208 are embedded upon implantation of IMD 200. The electronic circuitry of IMD 200 may be configured to generate and deliver electrical pulse therapy to the tissue proximate to deep tines 208 via an electrode formed by a portion of deep tines 208, through the tissue, to return electrode 211. Each of deep tines 208 may include one or more sections, such as an elastically deformable material preset into one or more curved sections and one or more optional substantially straight sections. Deep tines 208 and shallow tines 210 may be formed to have a preset deployed shape and may be superelastic, e.g., made of the nickel-titanium alloy Nitinol.

The distal electrode portion(s) of deep tines 208 may be spaced apart from the distal end 213 of housing 204, and may be coupled to the sensing and therapy delivery circuitry by one or more conductors of a hermetic feedthrough assembly (not shown). In some examples, IMD 200 includes a retrieval structure 212 fixedly attached to or formed integrally with proximal end 214 of housing 204. Retrieval structure 212 may be configured for temporarily tethering IMD 200 to a delivery catheter or a retrieval catheter, such as delivery tool 106. In some examples, retrieval structure 212 may be configured to couple to tether assemblies, such as those described in provisional U.S. Patent Application No. 62/844,674, entitled "TETHER ASSEMBLIES FOR MEDICAL DEVICE DELIVERY SYSTEMS," the entire content of which is incorporated herein by reference.

Shallow tines 210 may be configured to hold deep tines 208 in contact with tissue at a target implant site, e.g., target implant site 102. A shape of each of shallow tines 210, and in some cases deep tines 208, may be selected to control deployment, tissue fixation, and/or tissue disengagement. For example, the shape of a respective tine may include a number of preset curves on the respective tine, a curvature (e.g., radius) of each preset curve on the respective tine, a length of each preset curve, a length of optional straight sections between preset curves, a width of the respective tine or sections thereof (e.g., one or more tapered portions), a thickness of the respective tine, a number of cutouts along the length of the respective tine, shapes of cutouts, or any combination thereof Shallow tines 210 may include one or more sections. For example, shallow tines 210 may include an elastically deformable material preset into one or more curved sections and one or more optional substantially straight sections. In some examples, shallow tines 210 may define a ribbon shape configured to deform along a plane normal to longitudinal axis 206 and resist twisting outside of the plane. In some examples, shallow tines 210 may include two or more curved sections (e.g., knuckles) as described in provisional U.S. Patent Application No. 62/825,233, entitled "FIXATION COMPONENTS FOR IMPLANTABLE MEDICAL DEVICES," the entire content of which is incorporated herein by reference. For example, one or both shallow tines 210 may be the same or substantially similar to tines described in U.S. Patent Application No. 62/825,233.

Shallow tines 210 may be configured to have a target deflection stiffness and a target deployment stiffness. The target deflection stiffness may include a measure of a resistance to force applied to IMD 200 in a proximal direction when deep tines 208 are engaged with tissue at target site 102. In some examples, the target deflection stiffness may be selected to enable shallow tines 210 to deflect a predetermined amount to enable visualization of shallow tines 210 under fluoroscopy.

In some examples, the target deflection stiffness may be within a range from about 0.2 N to about 0.8 N, such as about 0.3 N to about 0.6 N. The deployment stiffness may include a measure of a force applied by shallow tines 210 as shallow tines 210 move from a deformed configuration to an undeformed configuration upon deployment of IMD 200 from distal opening 108 of delivery tool 106 (FIG. 1) such that the free distal end of deep tines 208 penetrates the atrial or ventricular myocardium. In some examples, the target deployment stiffness may be within a range from about 0.6 N to about 1.2 N. FIG. 2A also illustrates marker 219, which in some examples may be a radiopaque marker. Marker 219 may be visible via medical imaging such as fluoroscopy, and allow a clinician to view and adjust the rotational orientation of IMD 200 to achieve a desired trajectory and/or a desired advancement path of deep tines 208 to target tissue.

Figure 2B:
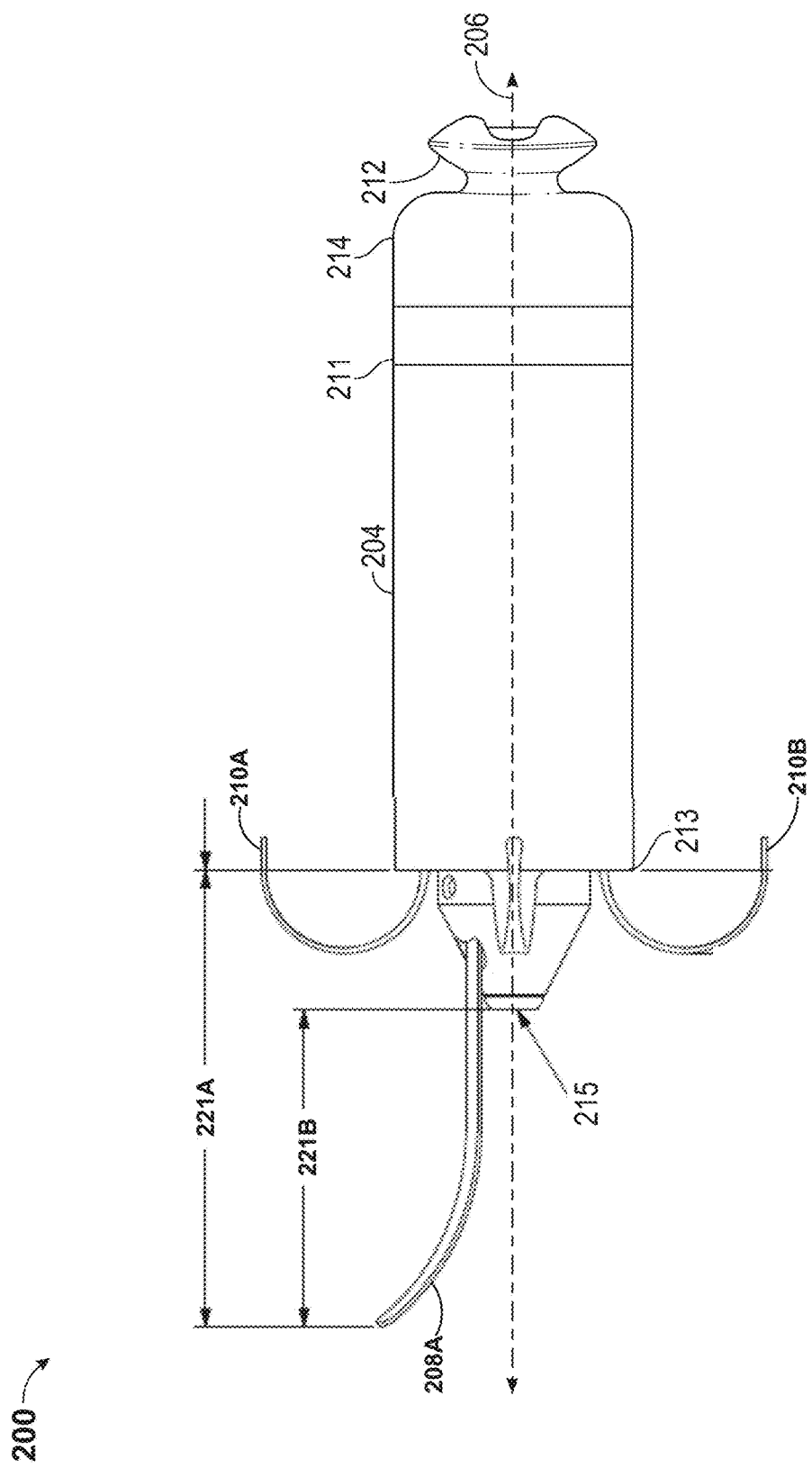
FIG. 2B illustrates an example dimensionality of the implementation of the IMD shown in FIG. 2A.

FIG. 2B illustrates an example dimensionality of the implementation of IMD 200 shown in FIG. 2A. Deep tine 210B is not shown in FIG. 2B for ease of illustration. FIG. 2B illustrates atrial electrode 215, which in various examples may be configured to enable atrial pacing and/or sensing. In some examples, shallow tines 210 may additionally or alternatively function as atrial electrode(s). Deep tine 208A may extend from atrial electrode 215 to a length denoted by distance 221B, may extend from distal end 213 of housing 204 to a length denoted by distance 221A. In various examples, distance 221B may be in a range of two to fifteen millimeters (mm), and distance 221A may be in a range of three to seventeen mm.

Figure 2C:
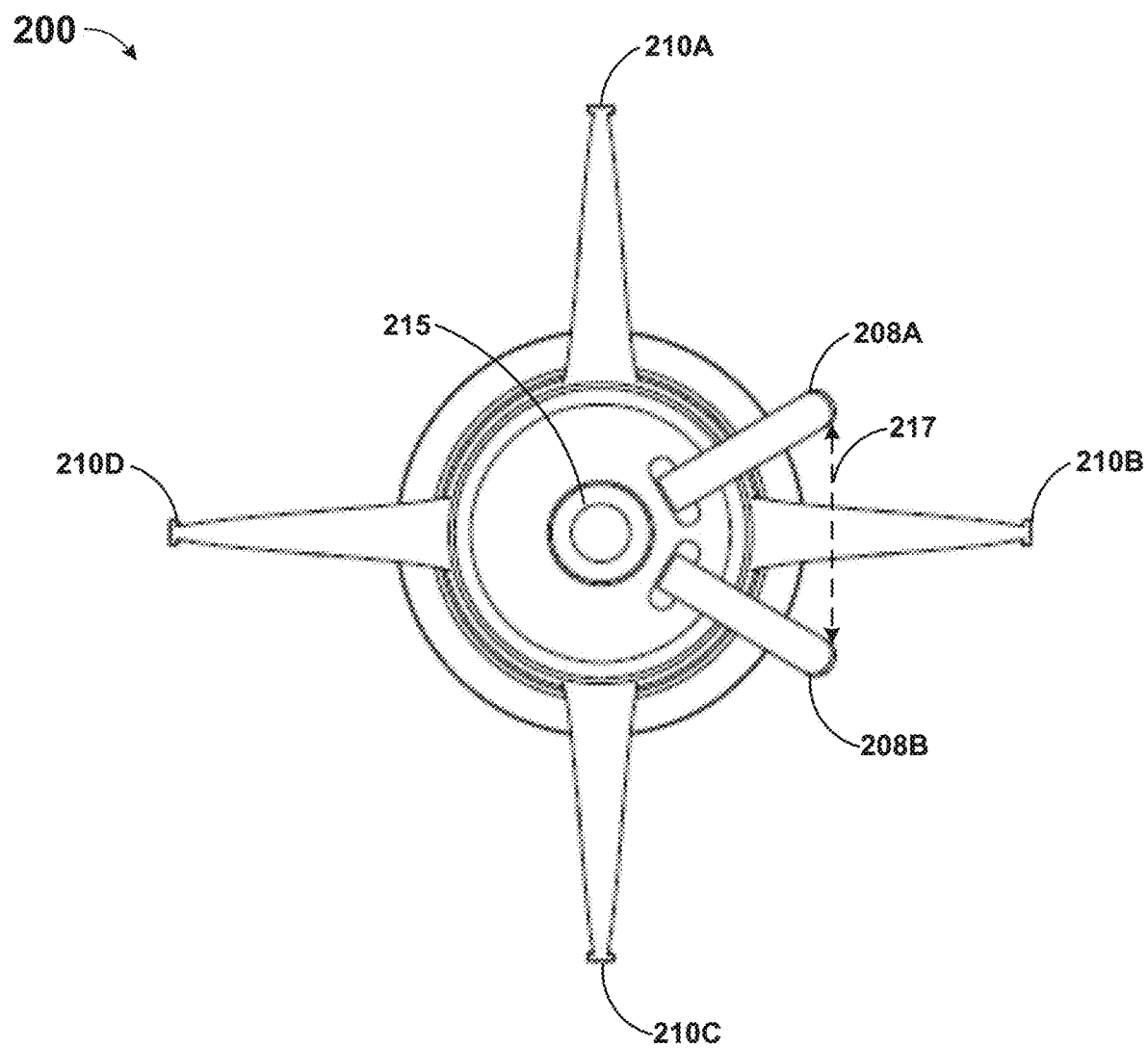
FIG. 2C illustrates an aerial view of the IMD shown in FIGS. 2A & 2B.

FIG. 2C illustrates an aerial or end view of IMD 200. In the example shown in FIG. 2C, IMD 200 includes four shallow tines 210 spaced equidistantly about a perimeter of IMD 200, although other number and spacing of shallow tines are contemplated. Deep tines 208A and 208B are spaced from each other at a distance 217, which may be expressed in angular units (e.g., degrees). In some examples, distance 217 may be in the range of 30 to 180 degrees. The illustrated number and arrangement of deep tines 208 in FIG. 2C is one non-limiting example, and IMD 200 may, in other examples consistent with this disclosure, include a greater number of deep tines 208 and/or a different position of deep tines 208 about longitudinal axis 206 of IMD 200. In one non-limiting example, deep tines 208 may include four deep tines equally distributed circumferentially.

Figure 2D:
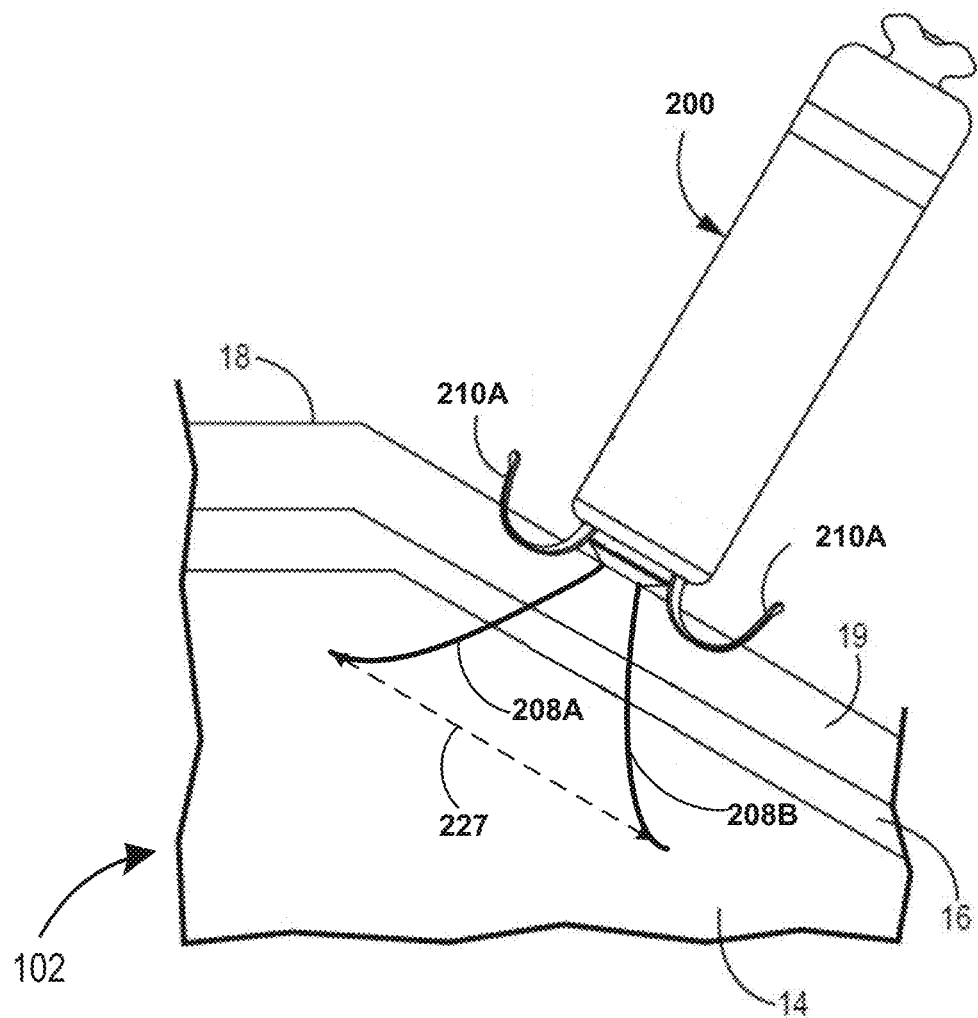
FIG. 2D is a conceptual diagram illustrating the IMD shown in FIGS. 2A-2C implanted at a target implant site.

FIG. 2D is a conceptual diagram illustrating IMD 200 implanted at target implant site 102. As shown in the implanted position of FIG. 2D, the distal tip of each of shallow tines 210 may exit back out of the atrial endocardial surface 18 such that tissue becomes engaged within the curved portion of each of shallow tines 210. As shallow tines 210 become engaged with the atrial myocardium 19, deep tines 208 pierce into the tissue at target implant site 102 and advance through the atrial myocardium 19 and central fibrous body 16 to position tip electrode 42 in the ventricular myocardium 14 as shown in FIG. 2D. Dislodgement of deep tines 208 out of the ventricular myocardium 14 is prevented by the undeformed configuration of shallow tines 210. If needed, deep tines 208, e.g., IMD 200 including deep tines 208 and shallow tines 210, may be recaptured using a catheter, or may be recaptured in another way.

The length of deep tines 208 is selected such that the tip electrode of each of deep tines 208 reaches an adequate depth in the tissue layers (e.g., the ventricular myocardium) to function as a stimulation electrode with respect to the HB or other target tissue, without puncturing all the way through into an adjacent cardiac chamber. In various implementations, the length of deep tines 208 may be at least 3 mm but less than 20 mm, less than 15 mm, less than 10 mm or up to 8 mm.

In some examples, the respective stimulation electrodes (tip electrodes) of deep tines 208 and the distal tips of shallow tines 210 may extend approximately equidistant from the distal end of housing 204. In this case, the tip electrodes of deep tines 208 and the distal tips of shallow tines 210 will pierce the tissue at target implant site 102 simultaneously as IMD 200 is advanced out of the distal opening. Manual pressure applied to the proximal end of housing 204 via an advancement tool provides the longitudinal force required to pierce the cardiac tissue at target implant site 102.

In other examples, the distal tips of shallow tines 210 may extend a length from the proximal base that is greater than the length of deep tines 208 when IMD 200 is held in an extended position within a receptacle. The distal tips of shallow tines 210 pierce the tissue first in this case (before the tip electrodes of deep tines 208), and may act to pull IMD 200 toward the atrial endocardial surface 18 as shallow tines 210 elastically bend or curve back into the curved position. This pulling force produced by shallow tines 210 may contribute to the longitudinal force that drives the tip electrode of deep tines 208 into the tissue at target implant site 102 and advances the tip electrodes toward the pacing site near the HB. In some examples, the pulling force produced by shallow tines 210 may drive the tip electrodes of deep tines 208 into the heart tissue to a desired depth to deliver HB pacing, thereby reducing the overall amount of implant force necessary.

In still other examples, the length of deep electrodes 208 may be greater than the distance to which the distal tips of shallow tines 210 extend when held in the extended position. In this case, the tip electrodes of deep tines 208 pierce the atrial endocardium first and advance partially into the tissue layers before the distal tips of shallow tines 210 enter the endocardial tissue. For instance, the tip electrodes of deep tines 208 may advance at least partially through the atrial myocardium and shallow tines 210 may act to increase the longitudinal force driving the tip electrodes of deep tines 208 through the central fibrous body and into the ventricular myocardium by pulling IMD 200 toward the atrial endocardial surface as shallow tines 210 elastically return to their normally curved positions. Distance 227 shows the distance between the distal tips of deep tines 208 after implantation. Distance 227 may be greater than distance 217 shown in FIG. 2C, in implementations in which deep tines 208 are designed and spaced to spread apart during or immediately after implantation. Shallow tines 210 may be angularly spaced in the range of 40 degrees to 180 degrees.

Figure 3A:
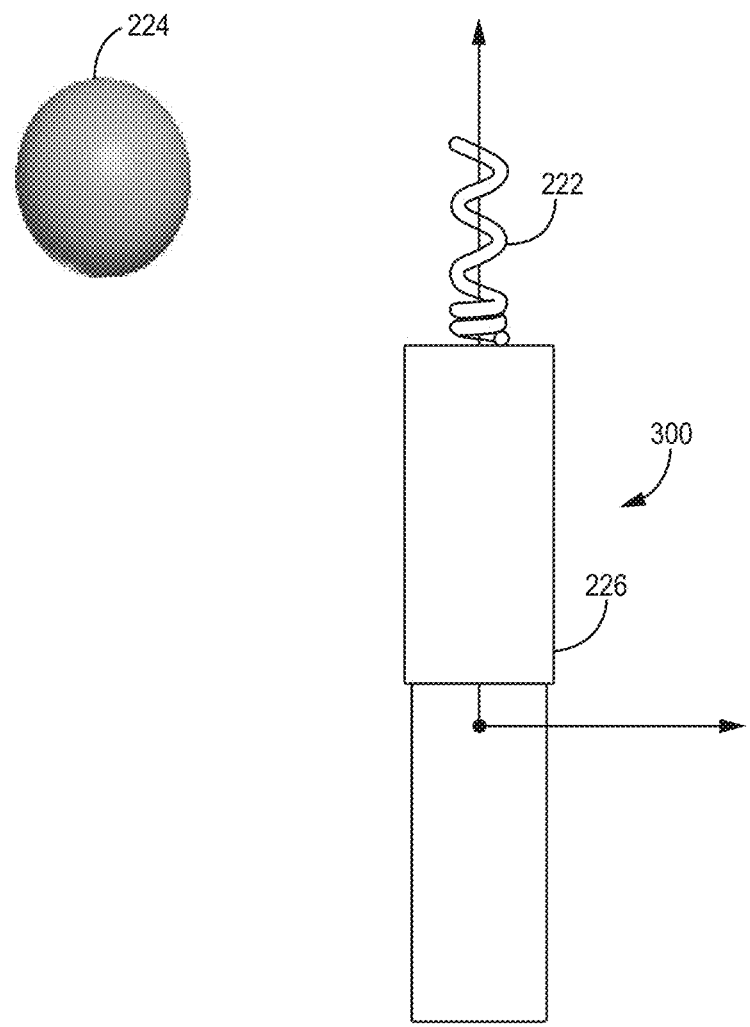
FIGS. 3A-3F illustrate various examples of IMDs including various electrode configurations according to aspects of this disclosure.

FIG. 3A illustrates another example IMD 300 including an electrode configuration according to aspects of this disclosure. In the example of FIG. 3A, IMD 300 includes a helical lead electrode 222 that provides pacing to HB 224 in tandem with ring return electrode 226. In one computer-modeled simulation, the peak electric field was observed with helical lead electrode 222 embedded in the septum and fixed at a position near HB 224, with ring return electrode 226 positioned in a respective chamber of the heart and as close as possible to the septum. In this computer-modeled simulation, the center of helical lead electrode 222 was positioned 0.25 inches from the center of HB 224. With 1V applied at helical lead electrode 222 and 0V applied at ring return electrode 226, the peak therapy electric field observed at HB 224 was 0.0557 V/cm (or 5.57 V/m).

Figure 3B:
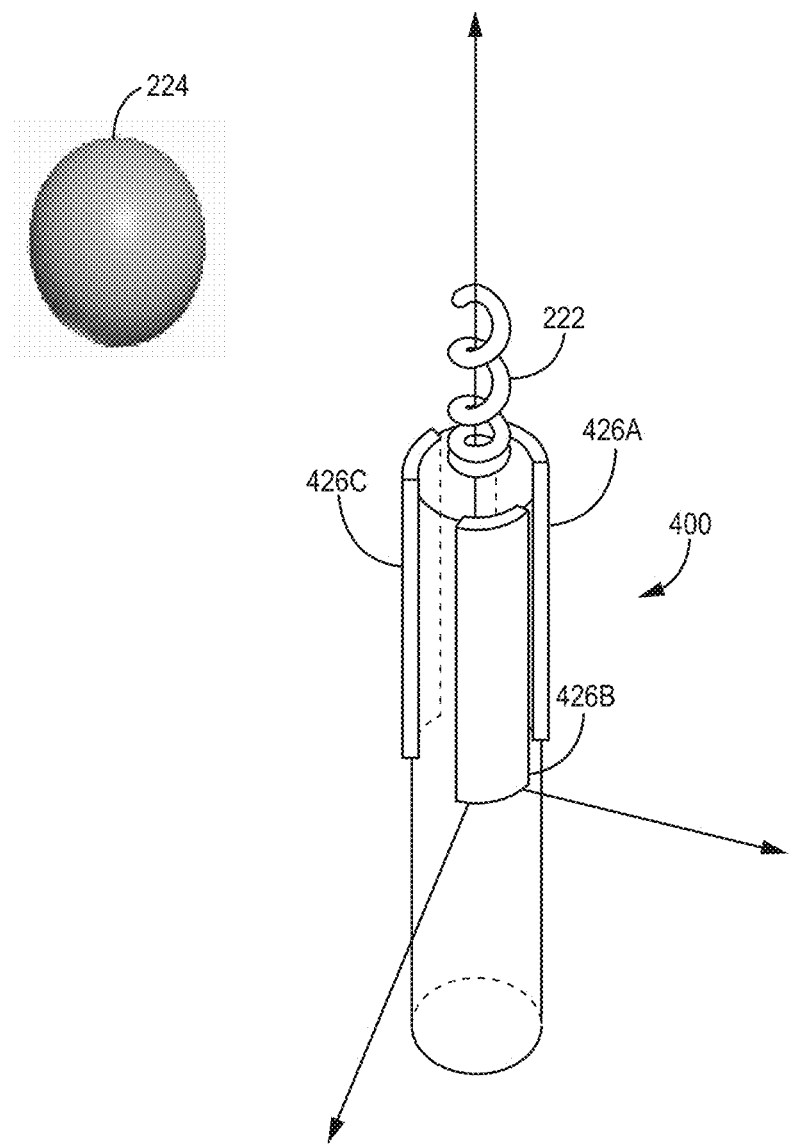

FIG. 3B illustrates another implementation of an IMD 400 according to aspects of this disclosure. In the implementation shown in FIG. 3B, IMD 400 includes helical lead electrode 222 as shown in FIG. 3A, which delivers His pacing to HB 224 in tandem with a segmented return electrode (which is also referred to as a "segmented ring electrode"), including electrode segments 426A, 426B, and 426C (collectively, "electrode segments 426"). The clinician may configure helical lead electrode 222 and one or more of electrode segments 426 to steer the electric field towards HB 224.

In the example illustrated in FIG. 3B, each respective electrode segment 426 covers 60 degrees of the circumference of IMD 400, with a 60-degree gap between every pair of segments 426. In one computer-modeled simulation, the active electrode segment 426 of the segmented return electrode was rotated around the center of the helix to observe the peak electric field in a HB 224 bundle, with 1V applied to helical lead electrode 222 and used 5-degree angular steps over a 360-degree region. The peak electric field obtained in this computer-modeled simulation was 0.0508 V/cm (or 5.08 V/m) when the active electrode segment 426 is closest to HB 224.

Figure 3C:
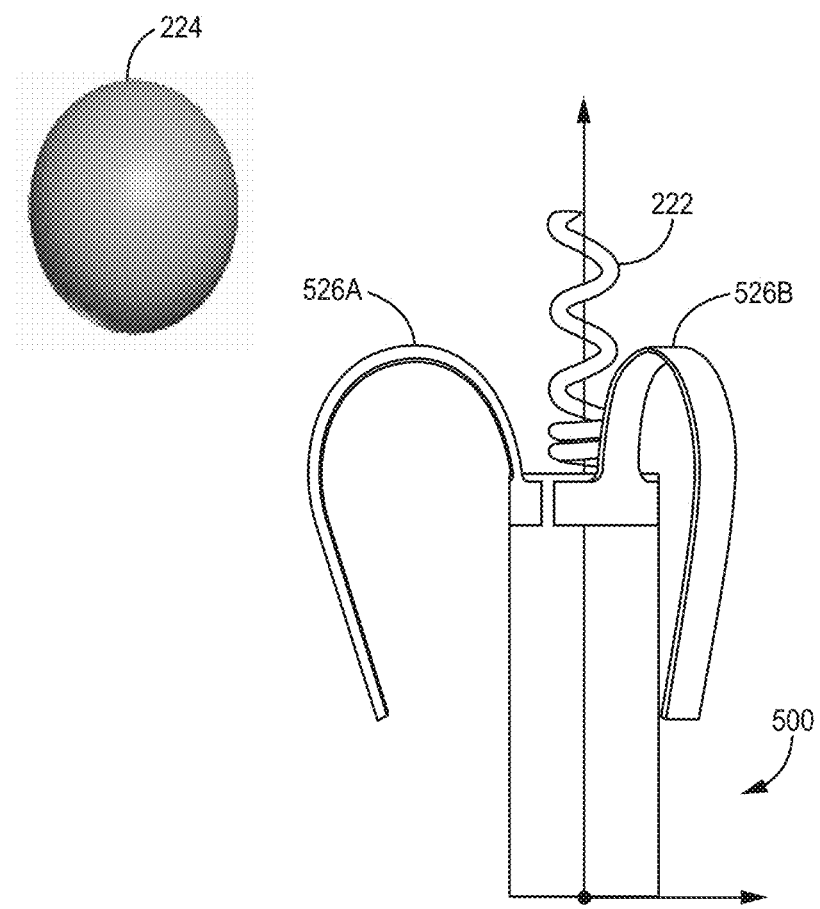

FIG. 3C illustrates another implementation of an IMD 500 according to aspects of this disclosure. In the implementation shown in FIG. 3C, IMD 500 includes helical lead electrode 222 as shown in FIGS. 3A & 3B, which delivers His pacing to HB 224 in tandem with tine return electrodes 526. FIG. 3C illustrates two tine electrodes, namely, tine return electrodes 526A and 526B. IMD 500 also includes a third tine return electrode, which is not visible in the view of IMD 500 shown in FIG. 3C. In various examples, IMD 500 may include any number of tine return electrodes 526 with any spacing therebetween.

In the illustrated example, tine return electrodes 526 are equally angularly spaced (i.e. at 120-degree intervals around the circumference of the distal end of IMD 500). All three of tine return electrodes 526 capture the septum and are 0.88 mm into the septum wall and located 250 mils from HB 224 in a computer-modeled simulation of the IMD 500 configuration shown in FIG. 3C. In the computer-modeled simulation, the active tine return electrode 526 was oriented at 180 degrees from HB 224. Applying 1V to helical lead electrode 222 and using 5-degree angular steps over a 360-degree region obtained a peak electric field of 0.5134 V/cm (or 51.34 V/m) when the active tine return electrode 526 is closest to HB 224.

In another computer-modeled simulation, the three tine return electrodes 526 were placed against the septal wall of the heart, thereby preventing possible bundle damage to HB 224 that might otherwise occur in septal-piercing placements. The computer-modeled simulation of this placement displayed a significant decrease in the electric field intensity in HB 224 (as compared to the septal-piercing placement). In this computer-modeled simulation, with 1V applied to helical lead electrode 222, the peak electric field observed at HB 224 was 0.123 V/cm (or 12.3 V/m). These results are approximately 25% of the electric field intensity computed in the computer-modeled simulation in which tine return electrodes 526 were positioned in a septal-piercing way.

Figure 3D:
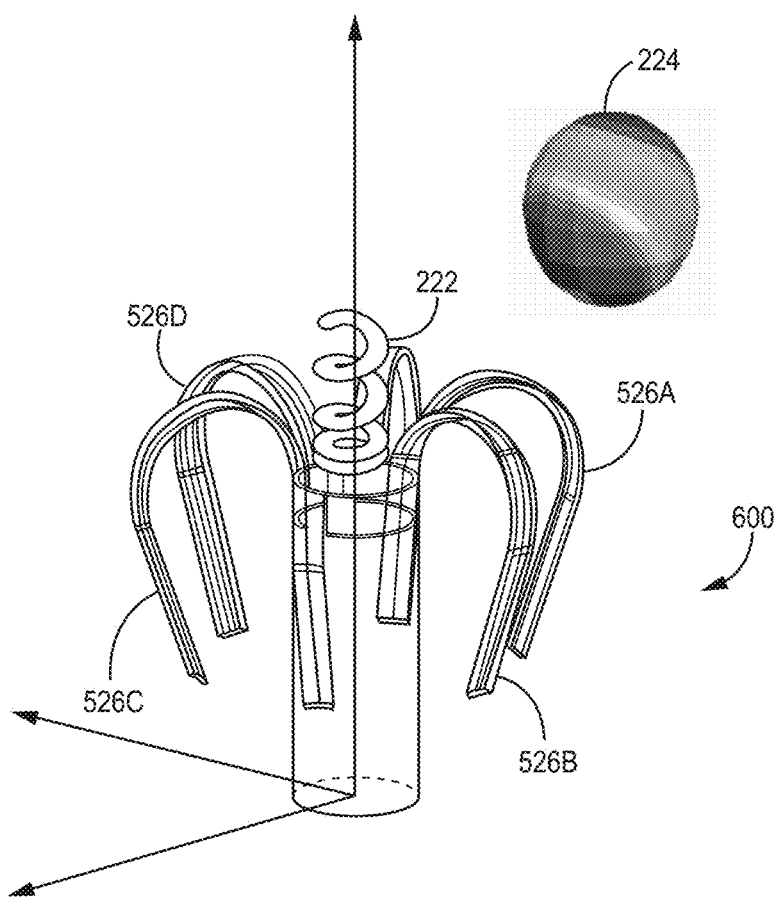

FIG. 3D illustrates another implementation of an IMD 600 according to aspects of this disclosure. In the implementation shown in FIG. 3D, IMD 200 includes helical lead electrode 222 as shown in FIGS. 3A-3C, which delivers His pacing to HB 224 in tandem with one or more of a total of six tine return electrodes 526. Only four of tine return electrodes 526 are labeled with reference numerals (526A-526D) in FIG. 3D, for ease of illustration.

In comparison to the implementation shown in FIG. 3C, the implementation of IMD 600 shown in FIG. 3D includes double the number of tine return electrodes 526. In some examples, tine return electrodes 526 are sorted into groupings of two electrically common tine return electrodes forming three total electrode groupings in tandem with helical lead electrode 222. The six tine return electrodes 526 are spaced equally (from an angular standpoint), with a 60-degree space between every adjacent pair of tine return electrodes 526 along the circumference of the distal end of IMD 600. Using the configuration shown in FIG. 3D, the clinician can capture a bundle of HB 224 anywhere within a half inch diameter circle about the distal end of IMD 600. The peak electric field observed with the configuration shown in FIG. 3D was 0.457 V/cm (or 45.7 V/m). Tine return electrodes 526 may, as depicted in FIGS. 3C and 3D, have a convex shape relative to the outer surface of the septum.

Figure 3E:
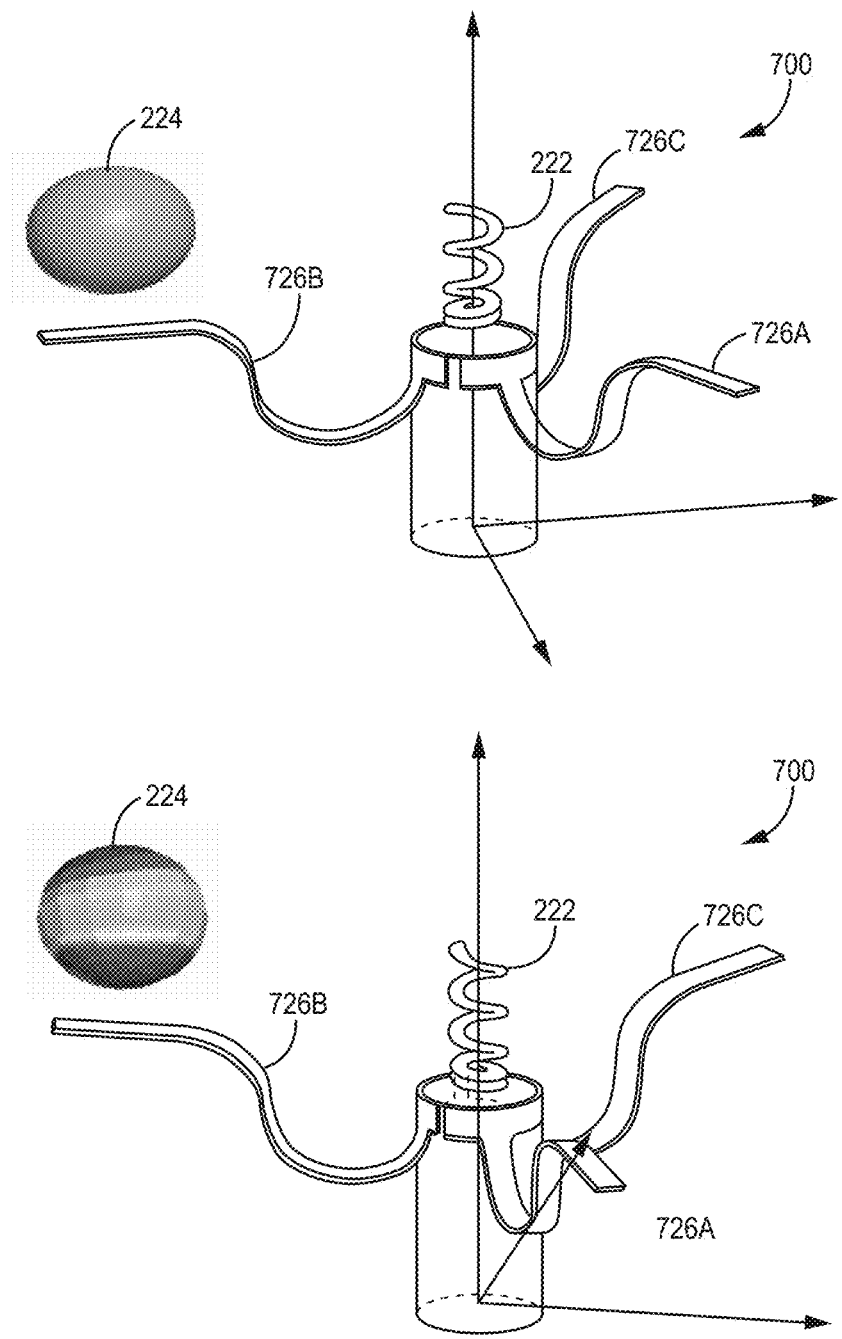

FIG. 3E illustrates views of another implementation of an IMD 700 according to aspects of this disclosure. In the implementation shown in FIG. 3E, IMD 200 includes helical lead electrode 222 as shown in FIGS. 3A-3D, which delivers His pacing to HB 224 in tandem with one or more of three inverted tine return electrodes 726A-726C (collectively "tine return electrodes 726"). The design of IMD 700 illustrated in FIG. 3E targets scenarios in which tines penetrating into the septal wall might not be desirable based on a chance the tines could damage HB 224 or one or more branches thereof. To prevent this potential His bundle damage in these scenarios, the design of IMD 700 shown in FIG. 3E incorporates inverted tine return electrodes 726 make contact with the septum in the way the bottom rim of an umbrella might rest on a flat or substantially flat surface.

Upon deployment of IMD 700 (if manufactured according to the design shown in FIG. 3E), inverted tine return electrodes 726 may make contact with the septum or other endocardial tissue without penetrating into the tissue. In a performance computer-modeled simulation, inverted tine return electrodes were limited to a 600 mil diameter circle outside the septum wall. With 1V applied to helical lead electrode 222, the peak electric field observed at HB 224 was 2.016 V/cm (or 201.6 V/m). The useful angular therapy coverage range was approximately 70 degrees for a single one of inverted tine return electrodes 726.

Figure 3F:
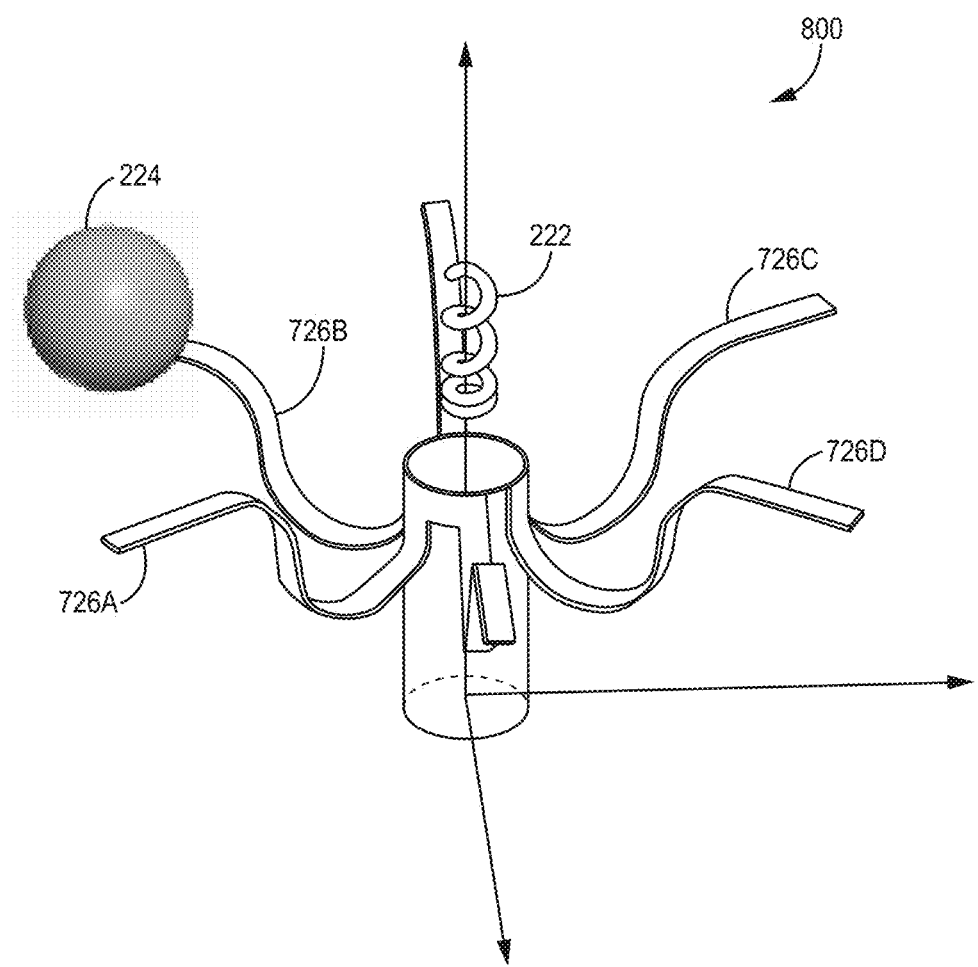

FIG. 3F illustrates another implementation of an IMD 800 according to aspects of this disclosure. In the implementation shown in FIG. 3F, IMD 800 includes helical lead electrode 222 as shown in FIGS. 3A-3E, which delivers His pacing to HB 224 in tandem with a total of six inverted tine return electrodes 726. Only four of inverted tine return electrodes 726, i.e., tine return electrodes 726A-726D, are labeled with reference numerals in FIG. 3F, for ease of illustration.

In comparison to the implementation shown in FIG. 3E, the implementation of IMD 800 shown in FIG. 3F includes double the number of tine return electrodes. In some examples, inverted tine return electrodes 726 are sorted into groupings of two electrically common inverted tine return electrodes 726 forming three total electrode groupings available for combination with with helical lead electrode 222. Using the configuration shown in FIG. 3F, the clinician can capture a bundle of HB 224 anywhere within a half inch diameter circle. The peak electric field observed with the configuration shown in FIG. 3F was approximately 1.7 V/m (or 170 V/cm). The results of the computer-modeled simulation indicate that an angular spacing of less than 60 degrees between adjacent inverted tine return electrodes 726 may be beneficial to reduce the null depths (which are described in further detail below). Tine return electrodes 726 may, as depicted in FIGS. 3C and 3D, have a concave shape relative to the outer surface of the septum.

In each of FIGS. 3A-3F, helical electrode 222 represents a deep electrode, while the respective return electrodes represent shallow electrodes. The deep electrode is configured to extend to a greater distance from the distal end of the respective IMD than the distance to which the shallow electrodes extend from the distal end of the respective IMD. When deployed in the target tissue (e.g., a cardiac septum), the deep electrode may extend further into the target tissue than the depth to which the shallow electrodes, in their respective deployed states (where applicable) extend into the target tissue. In some examples, the deep electrode may pierce through or penetrate the entire thickness of the target tissue, potentially reaching a heart chamber opposite the septum from the chamber of implantation of the IMD, while the shallow electrodes (in their respective deformed states, where applicable) may pierce the septum partially without reaching the chamber opposite the septum from the chamber of implantation of the IMD.

Figure 4A:
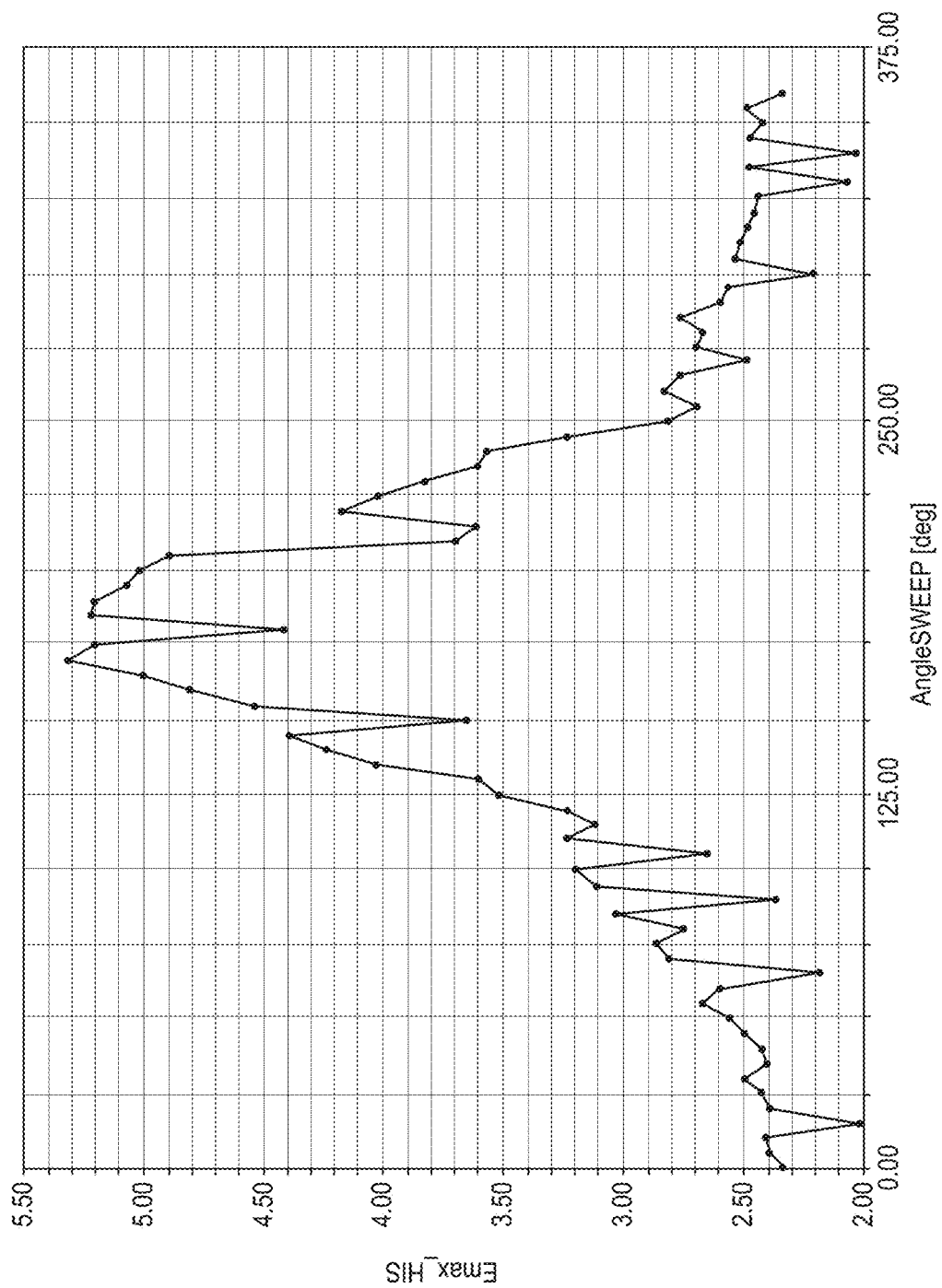

FIG. 4A is a graph illustrating electric field variance at HB 224 as a function of angular sweeps in a computer-modeled simulation done on the configuration of IMD 400 shown in FIG. 3B with the segmented return electrode comprises electrode segments 426. As described above with respect to FIG. 3B, the peak electric field obtained in this computer-modeled simulation was 0.0508 V/cm (or 5.08 V/m) when the active electrode (i.e. the active segment 426 of the segmented return electrode) is closest to HB 224.

Figure 4B:
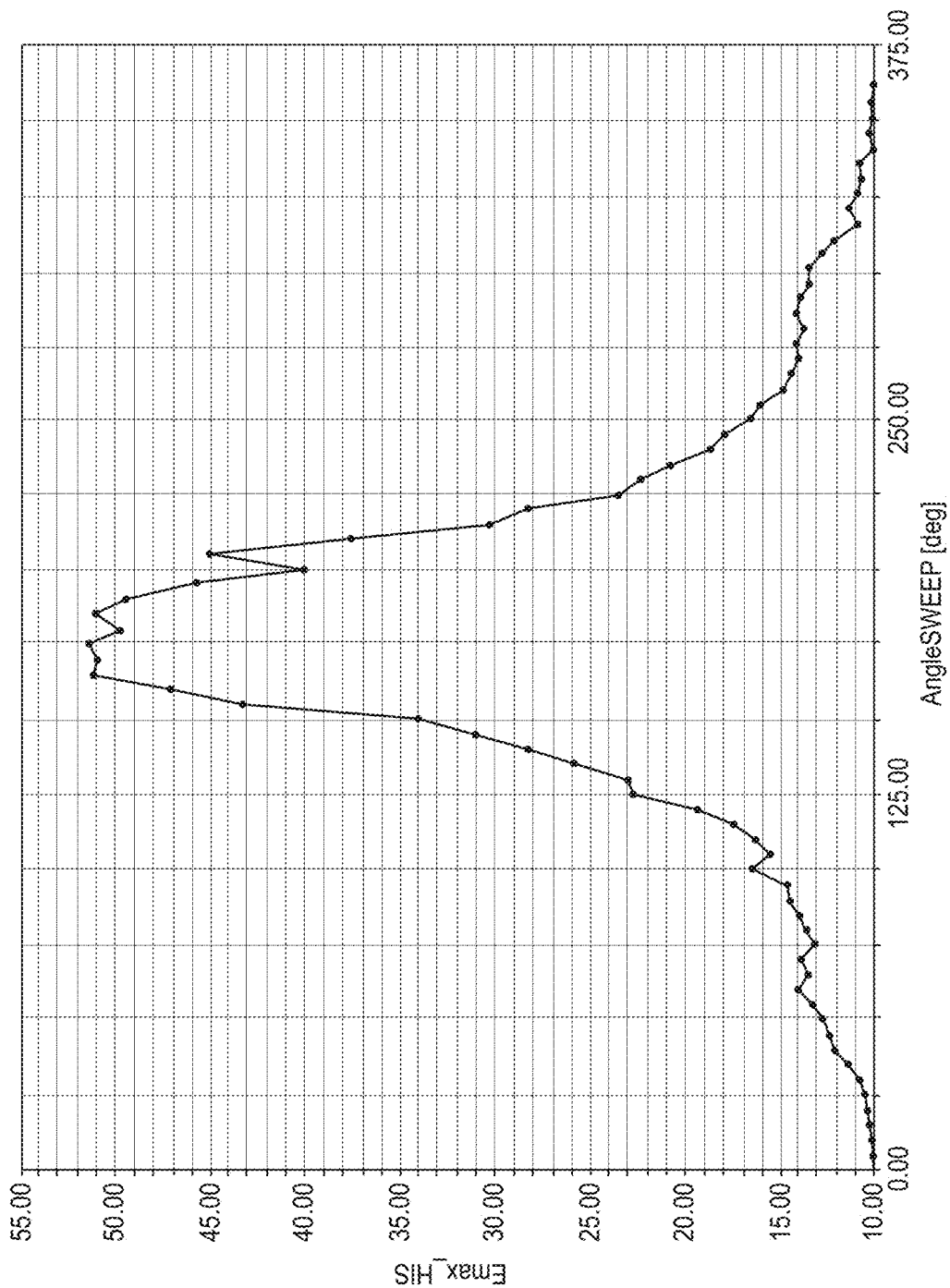

FIG. 4B is a graph illustrating electric field variance at HB 224 as a function of angular sweeps in a computer-modeled simulation done on the configuration of IMD 500 shown in FIG. 3C with three tine return electrodes 526. As described above with respect to FIG. 3C, the peak electric field obtained in this computer-modeled simulation was 0.5134 V/cm (or 51.34 V/m) when the active tine return electrode 526) is closest to HB 224. The plot of FIG. 4B shows that for each of tine return electrodes 526, there is approximately a 60-degree radial section of space thereabout that shows a significantly improved peak electric field in HB 224.

FIG. 4C is a graph illustrating electric field variance at HB 224 as a function of angular sweeps in a computer-modeled simulation done on the configuration of IMD 500 shown in FIG. 3C with three tine return electrodes 526, when positioned with tine return electrodes 526 making non-invasive contact with the septum. This alternate placement of IMD 500 manufactured according to the design of FIG. 3C exhibited a significant decrease in the electric field intensity in HB 224 with 1V applied to helical lead electrode 224. As described above with respect to FIG. 3C, with 1V applied to helical lead electrode 222 with tine return electrodes making only non-invasive contact with the septum, the peak electric field observed at HB 224 was 0.123 V/cm (or 12.3 V/m). These results are approximately 25% of the electric field intensity computed in the computer-modeled simulation in which tine return electrodes 526 were positioned in a septal-piercing way.

Figure 4D:
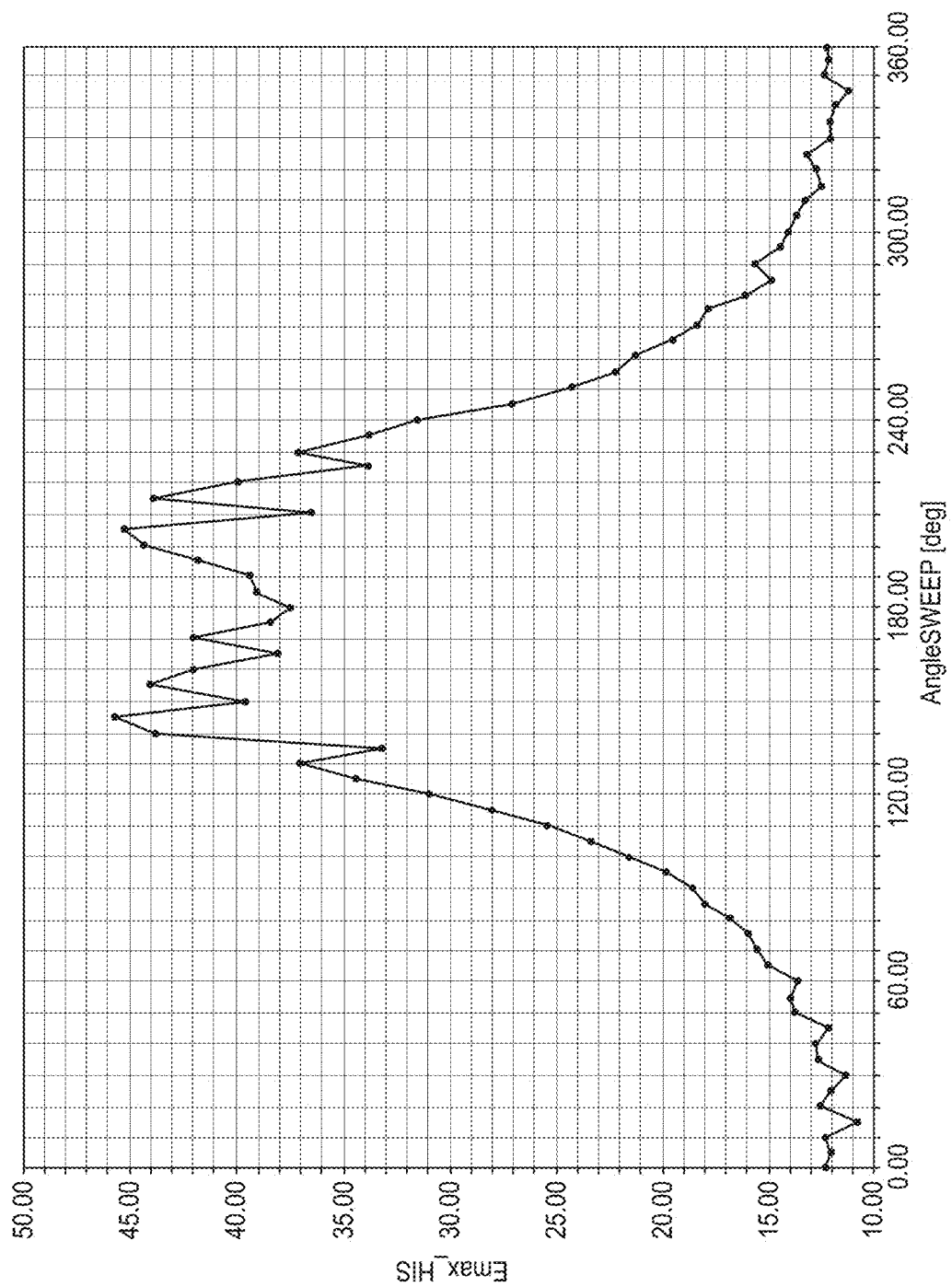

FIG. 4D is a graph illustrating electric field variance at HB 224 as a function of angular sweeps in a computer-modeled simulation done on the configuration of IMD 600 shown in FIG. 3D with six tine return electrodes 526. The peak electric field observed with the configuration shown in FIG. 3D was 0.457 V/cm (or 45.7 V/m), as shown by the peak value shown in the graph of FIG. 4D.

Figure 4E:
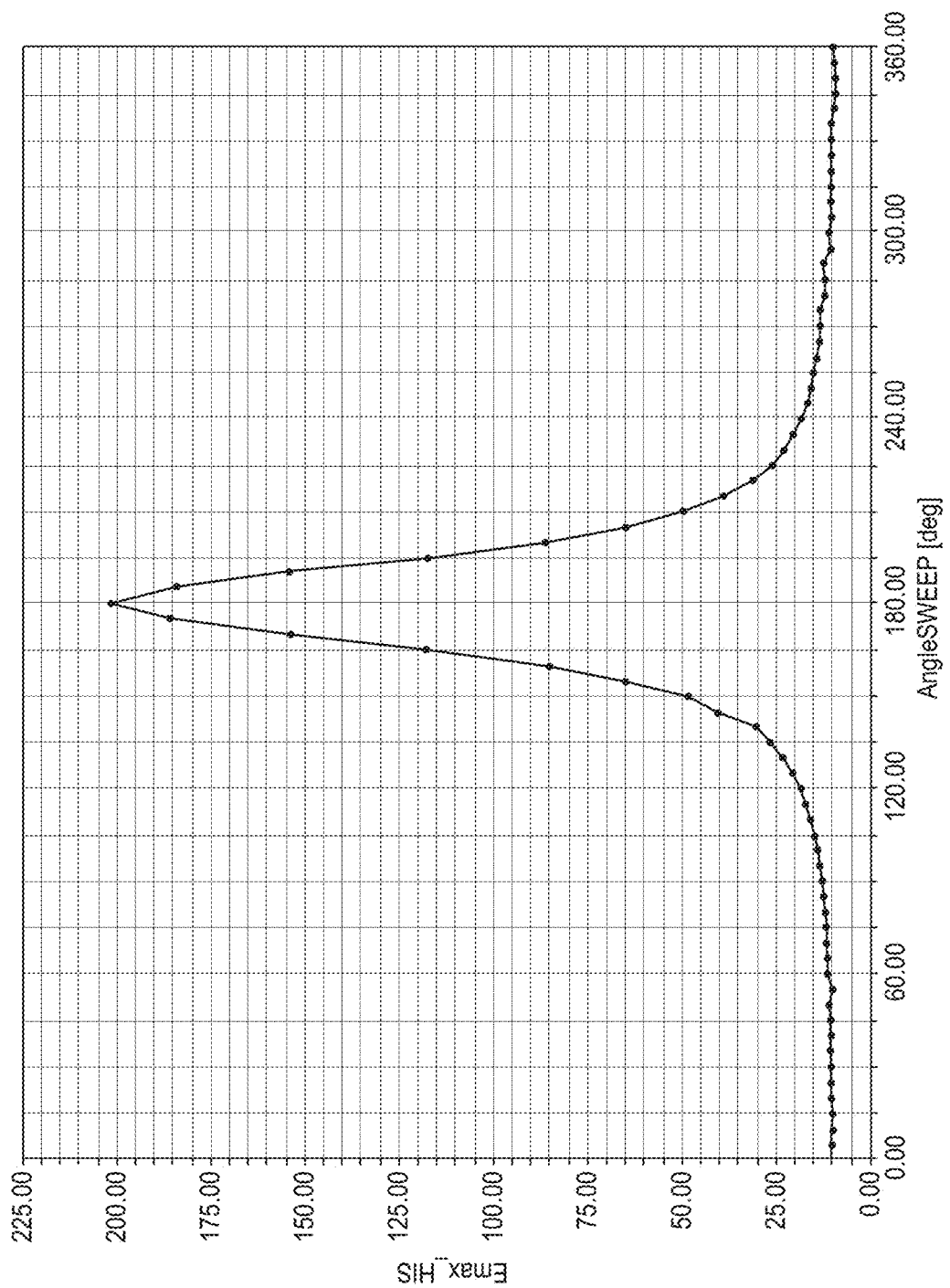

FIG. 4E is a graph illustrating electric field variance at HB 224 as a function of angular sweeps in a computer-modeled simulation done on the configuration of IMD 700 shown in FIG. 3E with three inverted tine return electrodes 726, positioned with inverted tine return electrodes 726 making non-invasive contact with the septum. With 1V applied to helical lead electrode 222, the peak electric field observed at HB 224 was 2.016 V/cm (or 201.6 V/m). The useful angular therapy coverage range r a single one of inverted tine return electrodes 726 was approximately a 70 angular degree range about the return electrode.

FIG. 4F is a graph illustrating electric field variance at HB 224 as a function of angular sweeps in a computer-modeled simulation done on the configuration of IMD 800 shown in FIG. 3F with six inverted tine return electrodes 726. The peak electric field observed with the configuration shown in FIG. 3F was approximately 1.7 V/m (or 170V/cm), as shown by the peak values shown in the graph of FIG. 4F. In the graph of FIG. 4F, there are two distinct peaks with a null (~0.4 v/m or 40 v/cm) between the inverted tine pair so an angular spacing less than 60 degrees may be beneficial to reduce the null depth.

Figure 5A:
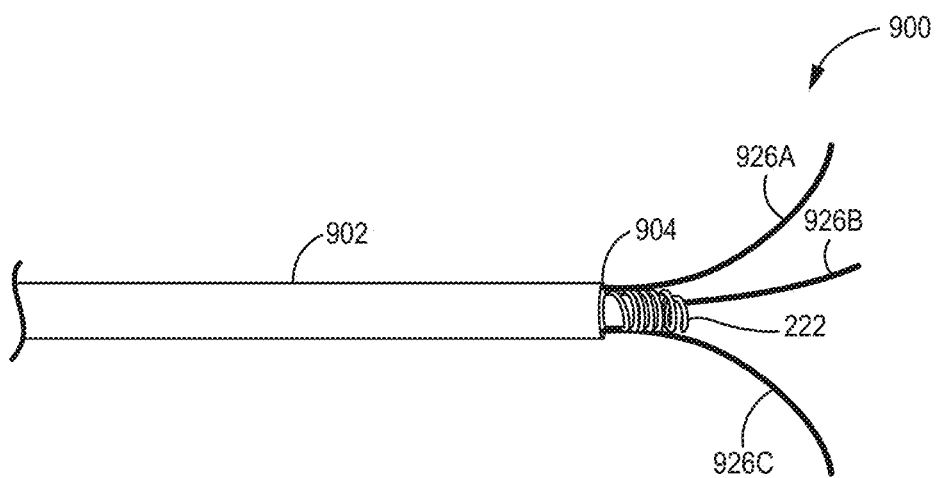
FIGS. 5A and 5B illustrate an example IMD that can be configured as a lead-in-lead system according to aspects of this disclosure.
Figure 5B:
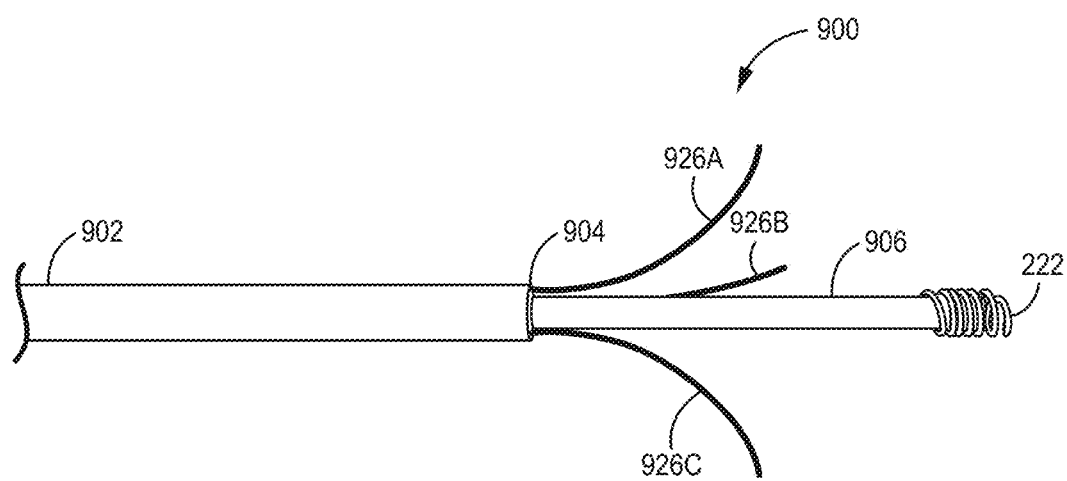

FIGS. 5A and 5B illustrate IMD 900 that can be configured as a lead-in-lead system according to aspects of this disclosure. Lead-in-lead systems allow the leads to be translatable or rotatable relative to one another to facilitate capturing desired parts of the patient's heart, such as septal tissue near HB 224, or other specific capture targets. Functioning as a lead-in-lead system, IMD 900 may provide a customized implantation solution for each patient.

IMD 900 includes an outer lead 902 and an inner lead 906. Inner lead 906 extends through an inner lumen (not shown) of outer lead 902. IMD 900 includes various conductors (not shown) operably coupled to electrodes. Any suitable conductors having the benefit of this disclosure may be used for extending through the implantable leads 902 and 906 of IMD 900 using any suitable techniques.

A plurality of deep tines 926A-926C (collectively, "deep tines 926") extend distally from distal end 904 of outer lead 902. Deep tines 926 may be formed similarly to and function (e.g., as electrodes) similarly to any of the deep tines described herein. Deep tines 926 may be fixedly attached to outer lead 902, or may be configured to be retracted into and extended from distal end 904 of outer lead 902. A shallow lead electrode 222, e.g., in the form of a helix in the illustrated example, is coupled to inner lead 906.

IMD 900 may be delivered to an implant site via a delivery catheter and/or sheath (not shown), which may constrain deep tines 926 is a pre-deployed configuration, e.g., extending distally substantially parallel to a longitudinal axis of IMD 900. When advanced from the delivery catheter and/or sheath, deep tines 926 may be released to a pre-configured, deployed configuration, and spread out laterally from each other as they penetrate the cardiac tissue. Shallow lead electrode 222 may be screwed or otherwise advanced into the cardiac tissue of the chamber into which IMD 900 is implanted. In some example implant procedures, shallow lead electrode 222 may be engaged first, leveraging the stability of this fixation to allows for an easier implant of deep tines (or "deep penetrating tines") 926. In some examples, IMD 900 may be implanted using a corresponding procedure, with the initial fixation step being made with an inner/outer lead with fixation tines instead of the helical implementation of shallow lead electrode 222 shown in FIGS. 5A & 5B.

Figure 6:
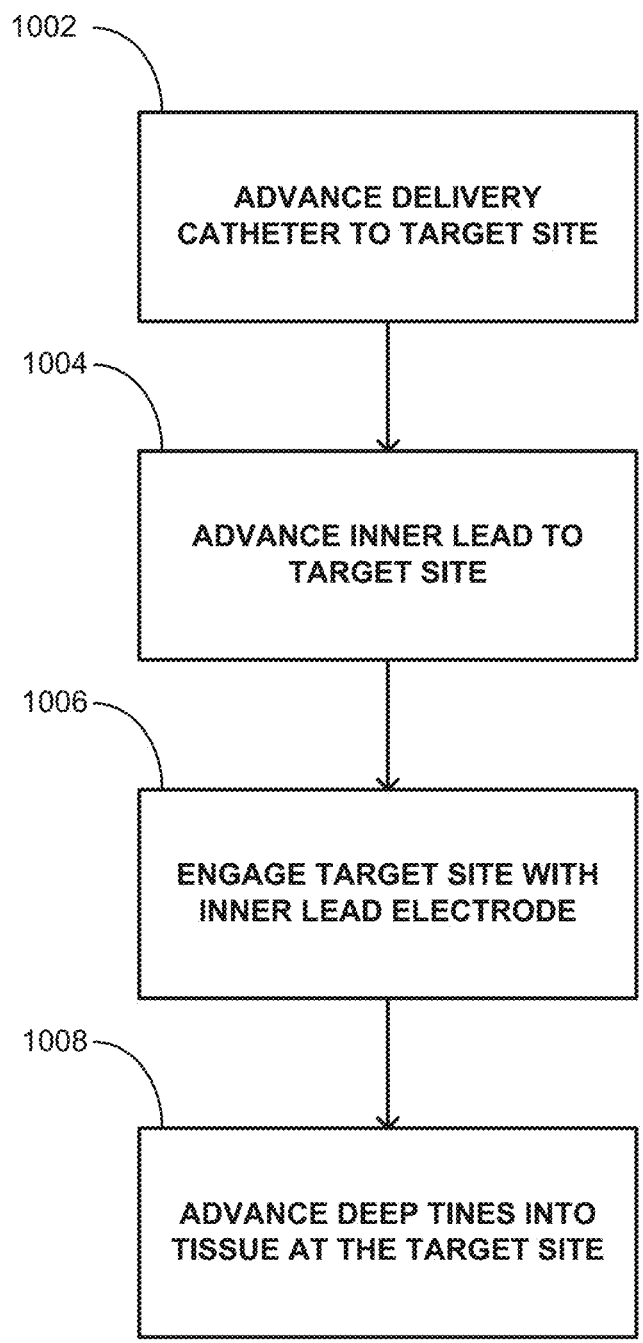
FIG. 6 is a flow diagram illustrating an example technique for implanting a lead-in-lead system according to aspects of this disclosure.

FIG. 6 is a flow diagram illustrating an example technique for implanting a lead-in-lead system according to aspects of this disclosure. The example technique of FIG. 6 is described in the context of IMD 900 of FIGS. 5A&5B, but may be applicable to other lead-in-lead systems. According to the example of FIG. 6, a delivery catheter or sheath used to guide the IMD 900 to a target implantation site in the heart is advanced to the target implantation site (1002). In some examples, the catheter is advanced to the target site with IMD 900 disposed in its delivery lumen. In other examples, the catheter is advanced over a guidewire and IMD 900 is then advanced through the lumen of the catheter.

According to the example of FIG. 6, inner lead 906 is advanced to the target implantation site (1004). In some examples, IMD 900 may be delivered with inner lead 906 already advanced to a distal end of the delivery catheter, while in others inner lead 906 may be retracted from the distal end of the delivery catheter, e.g., to protect patient tissue from electrode 222 during navigation to the target implantation site. Electrode 222 engages the target implantation site (1006). For example, inner lead 906 may be advanced and rotated to advance electrode 222 out of the distal end of the delivery catheter and screw electrode 222 into tissue at the target implantation site.

According to the example of FIG. 6, deep tines 926 are advanced out of the distal end of the delivery catheter through the tissue at the target implantation site and into to deeper tissue, such as tissue near the HB or other conduction system tissues of the heart (1008). For example, outer lead 902 may be advanced over inner lead 906 to advance deep tines 926 out of the distal opening. As discussed herein, deep tines 926 may be constrained by the delivery catheter and achieved a deployed shape, including spacing from each other, when advanced out of the catheter and into tissue.

The following examples are illustrative of the techniques described herein.

Example 1A: An implantable medical device (IMD) comprising: a plurality of deep tines configured to be advanced into a septum of a heart of a patient in different directions that are not parallel to a longitudinal axis of the implantable medical device, wherein each of the plurality of tines is configured to deliver cardiac pacing to cardiac tissue distal to a chamber of the heart in which the IMD is implanted; and one or more shallow electrodes engageable with the septum, wherein the one or more shallow electrodes are configured to deliver cardiac pacing to the chamber of the heart in which the IMD is implanted.

Example 2A: The IMD of example 1A, wherein the one or more shallow electrodes are configured to deliver atrial pacing therapy.

Example 3A: The IMD of example 1A, wherein the one or more deep tines are configured to deliver ventricular pacing therapy.

Example 4A: The IMD of any of examples 1A-3A, wherein the deep tines are configured to be advanced into the septum up to a ventricular myocardium of the heart of the patient.

Example 5A: The IMD of any of examples 1A-4A, wherein the plurality of deep tines are configured to deliver cardiac pacing to a bundle of His (HB) of the heart of the patient.

Example 6A: The IMD of example 5A, wherein the plurality of deep tines are configured to deliver the cardiac pacing to at least one of a left bundle branch (LBB) or a right bundle branch (RBB) of the HB of the heart of the patient.

Example 7A: The IMD of any of examples 1A-6A, wherein the plurality of deep tines are configured to be advanced into the septum by piercing the septum.

Example 8A: The IMD of any of examples 1A-7A, wherein the plurality of shallow electrodes are engageable with the septum via piercing of the septum.

Example 9A: The IMD of example 8A, wherein the plurality of shallow electrodes comprise respective shallow tines that, when in a deformed state, pierce the septum to a first depth that is less than a second depth to which the plurality of deep tines are configured to advance into the septum.

Example 10A: The IMD of any of examples 1A-9A, wherein the plurality of shallow electrodes are engageable with the septum via non-invasive physical contact with an outer surface of the septum.

Example 11A: The IMD of any of examples 1A-10A, wherein each deep tine of the plurality of deep tines is individually selectable to deliver the cardiac pacing in combination with at least a subset of the plurality of shallow electrodes.

Example 12A: The IMD of any of examples 1A-11A, wherein a spacing between adjacent deep tines of the plurality of deep tines is in a range from 30 degrees to 180 degrees.

Example 1B: An implantable medical device (IMD) comprising: a deep electrode that is configured to be advanced into a septum of a heart of a patient; and a plurality of shallow tines engageable with the septum, a subset of the plurality of shallow tines being selectable to form one or more return electrodes configured to deliver, in tandem with the helical lead electrode, pacing therapy to a target site within the septum.

Example 2B: The IMD of example 1B, wherein the deep electrode comprises a helical lead electrode.

Example 3B: The IMD of example 1B, wherein the pacing therapy comprises ventricular pacing therapy.

Example 4B: The IMD of any of examples 1B-3B, wherein the deep electrode is configured to be advanced into the septum up to a ventricular myocardium of the heart of the patient.

Example 5B: The IMD of any of examples 1B-4B, wherein the target site comprises a bundle of His (HB) of the heart of the patient.

Example 6B: The IMD of example 5B, wherein the deep electrode is configured to deliver the cardiac pacing to at least one of a left bundle branch (LBB) or a right bundle branch (RBB) of the HB of the heart of the patient.

Example 7B: The IMD of any of examples 1B-6B, wherein the deep electrode is configured to be advanced into the septum by piercing the septum.

Example 8B: The IMD of example 7B, wherein the plurality of shallow tines are engageable with the septum via piercing of the septum.

Example 9B: The IMD of example 8B, wherein the plurality of shallow tines, when in a deformed state, pierce the septum to a first depth that is less than a second depth to which the deep electrode pierce the septum.

Example 10B: The IMD of any of examples 1B-7B, wherein the plurality of shallow tines are engageable with the septum via non-invasive physical contact with an outer surface of the septum.

Example 11B: The IMD of example 10B, wherein the plurality of shallow tines, when in respective deformed positions, are convex with respect to the outer surface of the septum.

Example 12B: The IMD of example 10B, wherein the plurality of shallow tines, when in respective deformed positions, are concave with respect to the outer surface of the septum.

Example 13B: The IMD of any of examples 1B-12B, wherein the plurality of shallow tines comprise a total of three (3) shallow tines.

Example 14B: The IMD of any of examples 1B-12B, wherein the plurality of shallow tines comprise a total of six (6) shallow tines.

Various examples of the disclosure have been described. Any combination of the described systems, operations, or functions is contemplated. These and other examples are within the scope of the following claims.

What is claimed is:

1. An implantable medical device (IMD) comprising:
a plurality of deep tines configured to be advanced into a septum of a heart of a patient in different directions that are not parallel to a longitudinal axis of the implantable medical device, wherein each deep tine of the plurality of deep tines is configured to deliver cardiac pacing to cardiac tissue distal to a chamber of the heart in which the IMD is implanted; and
one or more shallow electrodes configured to transition from a deformed state to an undeformed state to engage with the septum, wherein the one or more shallow electrodes are configured to deliver cardiac pacing to the chamber of the heart in which the IMD is implanted.

2. The IMD of claim 1, wherein the one or more shallow electrodes are configured to deliver atrial pacing therapy, and the deep tines are configured to deliver ventricular pacing therapy.

3. The IMD of claim 1, wherein the deep tines are configured to be advanced into the septum to a ventricular myocardium of the heart of the patient.

4. The IMD claim 1, wherein the plurality of deep tines are configured to deliver the cardiac pacing to at least one of a left bundle branch (LBB), a right bundle branch (RBB), or a bundle of His (HB) of the heart of the patient.

5. The IMD of claim 1, wherein the one or more shallow electrodes comprise a plurality of shallow tines that, when in the undeformed state, are configured to pierce the septum to a first depth that is less than a second depth to which the plurality of deep tines are configured to advance into the septum.

6. The IMD of claim 1, wherein each deep tine of the plurality of deep tines is individually selectable to deliver the cardiac pacing in combination with at least one of the one or more shallow electrodes.

7. The IMD of claim 1, wherein a spacing between adjacent deep tines of the plurality of deep tines is in a range from 30 degrees to 180 degrees.

8. The IMD of claim 1, further comprising:
an outer lead comprising a lumen, wherein the plurality of deep tines extend from a distal end of the outer lead; and
an inner lead configured to be movable within the lumen of the outer lead, wherein the one or more shallow electrodes are located at a distal end of the inner lead.

9. The IMD of claim 1, wherein the one or more shallow electrodes are configured to transform from the deformed configuration in an undeployed state to the undeformed configuration in a deployed state.

10. The IMD of claim 9, wherein each electrode of the one or more shallow electrodes comprises an elastically deformable material defining a preset deployed shape.

* * * * *